United States Patent [19]

Tone et al.

[11] Patent Number: 5,459,142
[45] Date of Patent: Oct. 17, 1995

[54] PYRAZINYL AND PIPERAZINYL SUBSTITUTED PYRAZINE COMPOUNDS

[75] Inventors: Hitoshi Tone; Seiji Sato; Katsumi Tamura, all of Tokushima; Hideaki Sato; Toshiki Miyazaki, both of Naruto; Yoshimasa Nakano, Tokushima, all of Japan

[73] Assignee: Otsuka Pharmaceutical Co., Ltd., Tokyo, Japan

[21] Appl. No.: 110,797

[22] Filed: Aug. 23, 1993

Related U.S. Application Data

[63] Continuation of Ser. No. 876,454, Apr. 30, 1992, abandoned.

[30] Foreign Application Priority Data

May 1, 1991 [JP] Japan ................................ 3-100049

[51] Int. Cl.$^6$ .................................................. A61K 31/495
[52] U.S. Cl. ...................... 514/252; 514/235.8; 514/253; 514/255; 544/58.6; 544/120; 544/357; 544/405; 544/408; 548/483
[58] Field of Search ............................ 514/252; 544/357, 544/408, 405

[56] References Cited

U.S. PATENT DOCUMENTS

| | | | |
|---|---|---|---|
| 3,388,127 | 6/1968 | Shen et al. | 514/253 |
| 4,041,032 | 8/1977 | Murakami | 544/357 |
| 4,894,453 | 6/1990 | Yaso | 544/357 |
| 5,175,144 | 12/1992 | Walser | 514/252 |
| 5,238,938 | 8/1993 | Tone et al. | 514/253 |

FOREIGN PATENT DOCUMENTS

| | | |
|---|---|---|
| 3421452 | 5/1986 | European Pat. Off. . |
| 0303250 | 2/1989 | European Pat. Off. . |
| 5888330 | 8/1978 | Japan . |
| 959895 | of 1982 | U.S.S.R. . |

OTHER PUBLICATIONS

Dorland's Illustrated Medical Dictionary, 26th Ed. Saunders, Philadelphia, 1981, p. 557.
Shah, S. Kidney International vol. 35 (1989) pp. 1093–1106.
Ohta et al. Chem. Abstr. vol. 115 Entry 136469k (1991).
J. Org. Chem., vol. 56, No. 16, pp. 4864–4867 (1991).
Tetrahedron Letter, vol. 32, No. 42, pp. 6019–6020 (1991).
J. Antibiot., vol. 44, No. 1, pp. 52–58 (1991).
Chem. Abstr. vol. 100, No. 19, 100:150675w (1984).
Chem. Pharm. Bull., vol. 29, No. 1, pp. 88–97 (1981).
J. Med. Chem., vol. 15, No. 2, pp. 164–168 (1972).
Gokturk J. C. S. Perkin I. pp. 953–959 (1982).
Kawahara, Phytochemistry, vol. 27, No. 9, pp. 3022–3024 (1988).
Chem. Pharm. Bull., vol. 28, No. 9, pp. 2720–2733 (1980).
Chem. Pharm. Bull., vol. 27, No. 12, pp. 2980–2987 (1979).
Ohta, Heterocycles, vol. 31, No. 9, pp. 1655–1662 (1990).
Arai Chem. Pharm. Bull., vol. 29, No. 6, pp. 1510–1517 (1981).
Kakinuma J. Antibiot., vol. 27, No. 10, pp. 733–737 (1974).
Schollkopf Liebigs Ann. Chem., No. 2, pp. 413–317 (1985).

*Primary Examiner*—Donald G. Daus
*Attorney, Agent, or Firm*—Finnegan, Henderson, Farabow, Garrett & Dunner

[57] ABSTRACT

Novel pyrazine derivatives represented by the formula (1) and salts thereof which possess inhibitory effect against superoxide radicals ($O_2^-$) released from the macrophage cells of guinea pig by stimulation, and also possess anti-albuminuria activity in Masugi nephritis.

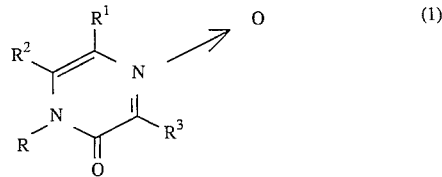

The pyrazine derivatives (1) and salts thereof are useful agents for preventing and treating of various diseases caused by the superoxide radicals, for example, diseases of autoimmune such as rheumatoid arthritis, arteriosclerosis, ischemic heart disease, transient cerebral ischematic attack, hepatic insufficiency, renal insufficiency and the like, as well as they are useful agents for preventing and treating the nephritis in various clinical fields.

13 Claims, No Drawings

PYRAZINYL AND PIPERAZINYL SUBSTITUTED PYRAZINE COMPOUNDS

This application is a continuation of application Ser. No. 07/876,454, filed Apr. 30, 1992, now abandoned.

FIELD OF THE INVENTION

The present invention relates to novel pyrazine derivatives and salts thereof. More particularly, the invention related to said pyrazine derivatives and salts thereof, processes for preparing the same, and a pharmaceutical composition containing, as the active ingredient, said pyrazine derivative or salt thereof.

PRIOR ART

There have been known certain prior art literatures as follows, which disclose compounds similar to and related to the pyrazine derivatives of the present invention, but the pharmacological activities of such known compounds are quite different from the pyrazine derivatives and salts thereof of the present invention.

(1) *J. Org. Chem.,* Vol. 56, No. 16, pp. 4864–4867, (1991)

(2) *Tetrahedron Letter,* Vol. 32, No. 42, pp. 6019–6020 (1991)

(3) *J. Antibiot.,* Vol. 44, No. 1, pp. 52–58, (1991)

(4) Japanese Patent Kokai (Laid-open) No. 53-88330 (1978), *Chem. Abstr.,* Vol. 100, No. 19, 100:150675w, (1984)

(5) *Chem. Pharm. Bull.,* Vol. 29, No. 1, pp. 88–97, (1981)

(6) *J. Med. Chem.,* Vol. 15, No. 2, pp. 164–168, (1972)

(7) USSR Patent No. 959895 (1982)

(8) *J. C. S. Perkin I.* pp. 953–959, (1982)

(9) *Phytochemistry,* Vol. 27, No. 9, pp. 3022–3024, (1988)

(10) *Chem. Pharm. Bull.,* Vol. 28, No. 9, pp. 2720–2733, (1980)

(11) *Chem, Pharm. Bull.,* Vol. 27, No. 12, pp. 2980–2987, (1979)

(12) *Heterocycles,* Vol. 31, No. 9, pp. 1655–1662, (1990)

(13) *Chem. Abstr.,* Vol. 95, No. 17: 150589z, *Chem. Pharm. Bull.,* Vol. 29, No. 6, pp. 1510–1517, (1981)

(14) *Chem. Abstr.,* Vol. 82, No. 23: 151872e, *J. Antibiot.,* Vol. 27, No. 10, pp. 733–737, (1974)

(15) *Chem. Abstr.,* Vol. 102, No. 25: 221162f, *Liebigs Ann. Chem.,* No. 2, pp. 413–417, (1985)

(16) EP-A1-181152 (Fujisawa Pharmaceutical Co., Ltd.) (May 14, 1986), Japanese Patent A2, 61-112060

(17) U.S. Pat. No. 3,388,127 (Merck & Co., Inc.) (Jan., 11, 1968)

(18) EP-A2-303250 (Otsuka Pharmaceutical Co., Ltd.) (Feb. 15, 1989), Japanese Patent A2, 01-177.

SUMMARY OF THE INVENTION

An object of the present invention is to provide novel pyrazine derivatives and salts thereof.

Another object of the present invention is to provide processes for preparing said pyrazine derivatives and salts thereof.

Further object of the present invention is to provide a pharmaceutical composition containing, as the active ingredient, said pyrazine derivative or salt thereof for preventing and treating diseases caused by superoxide radical.

DETAILED DESCRIPTION OF THE PREFERRED EMBODIMENTS

The novel pyrazine derivatives and salts thereof according to the present invention are represented by the formula (1),

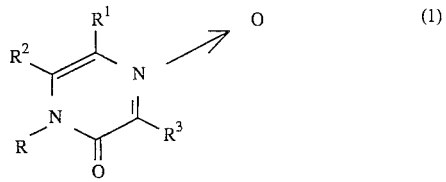

wherein R is a hydrogen atom or a lower alkyl group;

$R^1$ is a lower alkoxy group, a lower alkyl group or a hydroxy group;

$R^3$ is a lower alkyl group, a phenyl group, a phenyl-lower alkyl group, a lower alkenyl group or an indolyl-lower alkyl group;

$R^2$ is a phenyl-lower alkyl group which may have, on the phenyl ring, 1 to 3 substituents selected from the group consisting of a lower alkoxy group, a phenyl-lower alkoxy group, a lower alkyl group and a hydroxy group; a group of the formula

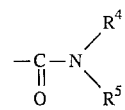

(wherein $R^4$ and $R^5$ are each the same or different from each other, and is a hydrogen atom, a cycloalkyl group; a lower alkyl group; a phenyl group which may have, on the phenyl ring, 1 to 3 substituents selected from the group consisting of a lower alkoxy group, a lower alkylthio group, a lower alkyl group, a hydroxy group and a phenyl group; a phenyl group having, on the phenyl ring, a lower alkylenedioxy groups as the substituents; a phenyl-lower alkyl group which may have, on the phenyl ring, 1 to 3 substituents selected from the group consisting of a lower alkoxy group, a phenyl-lower alkoxy group, a hydroxy group, a lower alkyl group and a halogen atom, further the alkyl moiety in said phenyl-lower alkyl group may have hydroxy groups as the substituents; a phenoxy-lower alkyl group which may have, on the phenyl ring, 1 to 3 lower alkoxy groups as the substituents;

a saturated or unsaturated 5- to 10-membered monocyclic or bicyclic heterocyclic residual group, having 1 to 2 hetero atoms selected from the group consisting of a nitrogen atom, an oxygen atom and a sulfur atom (said heterocyclic group may have a lower alkoxy group or an oxo group as the substituent);

a saturated or unsaturated 5- to 10-membered monocyclic or bicyclic heterocyclic-substituted lower alkyl group, in which the heterocyclic moiety having 1 to 2 hetero atoms selected from the group consisting of a nitrogen atom, an oxygen atom and a sulfur atom (said heterocyclic moiety may have a lower alkoxycarbonyl group or an oxo group as the substituent, further the lower alkyl moiety may have a carboxy group, a benzothiazolylaminocarbonyl group or a lower alkoxycarbonyl group as the substituent);

a 2,3-dihydroindenyl group which may have 1 to 5 substituents selected from the group consisting of a hydroxy group and a lower alkyl group;

further $R^4$ and $R^5$ form 5- or 6-membered saturated heterocyclic group by combining the nitrogen atom to which $R^4$ and $R^5$ are directly bonded thereto, together with or without other nitrogen atoms, oxygen atoms or sulfur atoms, said heterocyclic moiety may have, as the substituents, an oxo group, a lower alkoxycarbonyl group, a pyridyl group, a pyrazinylcarbonyl group which may have 1 to 4 substituents selected from the group consisting of an oxo group and a lower alkyl group, on the pyrazine ring;

a phenyl group which may have, on the phenyl ring, 1 to 3 substituents selected from the group consisting of a lower alkoxy group, a lower alkyl group and a lower alkanoyl group;

a benzoyl group which may have, on the phenyl ring, 1 to 3 substituents selected from the group consisting of a lower alkoxy group and a hydroxy group;

a benzoyl group having, on the phenyl ring, a lower alkylenedioxy groups as the substituents;

a phenyl-lower alkyl group which may have 1 to 3 substituents selected from the group consisting of a lower alkoxy group and a halogen atom; or a phenyl-lower alkenylcarbony group which may have, on the phenyl ring, 1 to 3 substituents group selected from the group consisting of a hydroxy group and a lower alkoxy group.)

The pyrazine derivatives and salts thereof represented by the formula (1) according to the present invention possess an inhibitory effect against superoxide radicals ($O_2^-$) released from the macrophage cells of guinea pig by stimulation, and also possess an anti-albuminuria activity in Masugi nephritis. Thus, the pyrazine derivatives and salts thereof represented by the formula (1) are useful agents for preventing and treating of various diseases caused by the abovementioned superoxide radicals, for example, diseases of autoimmune such as rheumatoid arthritis, arteriosclerosis, ischemic heart disease, transient cerebral ischematic attack, hepatic insufficiency, renal insufficiency and the like, as well as useful agents for preventing and treating the nephritis in various clinical fields. In addition to the above, a compound represented by the formula (2) and its lower alkyl ester are useful as intermediates for preparing the pyrazine derivatives represented by the formula (1) as above, and also possess the above-mentioned pharmacological activities and useful agents for the same purposes.

Each one of the substituents being indicated in the formula (1) is exemplified more specifically as follows:

The lower alkoxy group means a straight chain or branched chain alkoxy group having 1 to 6 carbon atoms, there can be exemplified methoxy, ethoxy, propoxy, isopropoxy, butoxy, tert-butoxy, pentyloxy and hexyloxy groups and the like.

The lower alkyl group means a straight chain or branched chain alkyl group having 1 to 6 carbon atoms, there can be exemplified methyl, ethyl, propyl, isopropyl, buty, tert-butyl, pentyl and hexyl groups and the like.

The cycloalkyl group means a cycloalkyl group having 3 to 8 carbon atoms, there can be exemplified cyclopropyl, cyclobutyl, cyclopentyl, cyclohexyl, cycloheptyl and cyclooctyl groups and the like.

The lower alkylthio group means a straight chain or branched chain alkylthio group having 1 to 6 carbon atoms, there can be exemplified methylthio, ethylthio, propylthio, isopropylthio, butylthio, tert-butylthio, gentylthio and hexylthio groups and the like.

The phenyl group which may have, on the phenyl ring, 1 to 3 substituents selected from the group consisting of a lower alkoxy group, a lower alkylthio group, a lower alkyl group, a hydroxy group and a phenyl group means, a phenyl group which may have, on the phenyl ring, 1 to 3 substituents selected from the group consisting of a straight chain or branched chain alkoxy group having 1 to 6 carbon atoms, a straight chain or branched chain alkylthio group having 1 to 6 carbon atoms, a straight chain or branched chain alkyl group having 1 to 6 carbon atoms, a hydroxy group and a phenyl group, there can be exemplified phenyl, 2-methoxyphenyl, 3-methoxyphenyl, 4-methoxyphenyl, 2-ethoxyphenyl, 3-ethoxyphenyl, 4-ethoxyphenyl, 3-isopropoxyphenyl, 4-hexyloxyphenyl, 3,4-dimethoxyphenyl, 2,5-dimethoxyphenyl, 3,4,5-trimethoxyphenyl, 2-methylthiophenyl, 3-methylthiophenyl, 4-methylthiophenyl, 2-ethylthyophenyl, 3-ethylthiophenyl, 4-ethylthiophenyl, 3-isopropylthiophenyl, 4-hexylthiophenyl, 3,4-dimethylthiophenyl, 2,5-dimethylthyophenyl, 3,4,5-trimethylthiophenyl, 2-methylphenyl, 3-methylphenyl, 4-methylphenyl, 2-ethylphenyl, 3-ethylphenyl, 4-ethylphenyl, 3-isopropylphenyl, 4-hexylphenyl, 3,4-dimethylphenyl, 2,5-dimethylphenyl, 3,4,5-trimethylphenyl, 3,5-di-tert-butyl-4-hydroxyphenyl, 2-hydroxyphenyl, 3-hydroxyphenyl, 4-hydroxyphenyl, 2,3-dihydroxyphenyl, 3,4-dihydroxyphenyl, 3,5-dihydroxyphenyl, 3,4,5-trihydroxyphenyl, 2-phenylphenyl, 3-phenylphenyl, 4-phenylphenyl, 2-methoxy-6-methylthiophenyl, 4-methyl-2-phenylphenyl groups and the like.

The phenyl group having, on the phenyl ring, lower alkylenedioxy groups as the substituents, means a phenyl group having, on the phenyl ring, straight chain or branched chain alkylenedioxy groups having 1 to 4 carbon atoms, there can be exemplified 3,4-methylenedioxyphenyl, 2,3-methylenedioxyphenyl, 2,3-ethylenedioxyphenyl, 3,4-trimethylenedioxyphenyl and 3,4-tetramethylenedioxyphenyl groups and the like.

The lower alkylenedioxy group means a straight chain or branched chain alkylenedioxy group having 1 to 4 carbon atoms, there can be exemplified methylenedioxy, ethylenedioxy, trimethylenedioxy and tetramethylenedioxy groups and the like.

The phenyl-lower alkyl group which may have, on the phenyl ring, 1 to 3 substituents selected from the group consisting of a lower alkoxy group, a phenyl-lower alkoxy group, a hydroxy group, a lower alkyl group and a halogen atom, further the lower alkyl moiety in said phenyl-lower alkyl group may have hydroxy groups as the substituents means, a phenyl-lower alkyl group in which the lower alkyl moiety is a straight chain or branched chain alkyl group having 1 to 6 carbon atoms, and may have hydroxy groups as the substituents, further, said phenyl-lower alkyl group which may have, on the phenyl ring, 1 to 3 substituents selected from the group consisting of a straight chain or branched chain alkoxy group having 1 to 6 carbon atoms, a phenyl-lower alkoxy group in which the alkoxy moiety therein is a straight chain or branched chain alkoxy group having 1 to 6 carbon atoms, a hydroxy group, a straight chain or branched chain alkyl group having 1 to 6 carbon atoms and a halogen atom, there can be exemplified benzyl, 2phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, diphenylmethyl, 2,2-diphenylethyl, 2-(3-methoxyphenyl)ethyl, 1-(4methoxyphenyl)ethyl, 2-methoxybenzyl, 3-(2-ethoxyphenyl) propyl,4-(3-ethoxyphenyl)butyl, 1,1-dimethyl-2-(4ethoxyphenyl)ethyl, 5-(4-isopropoxyphenyl)pentyl, 6-(4-hexyloxy- phenyl)hexyl, 3,4-dimethoxybenzyl, 3,4, 5trimethoxybenzyl, 2,5-dimethoxybenzyl, 1-phenyl-1-hydroxymethyl, 2-hydroxy-2-phenylethyl, 3-hydroxy-3-phenylpropyl, 4-hydroxy-4-phenylbutyl, 1.1-dimethyl-2-hydroxy- 2-phenylethyl, 5-hydroxy-5-phenylpentyl, 6-phenyl- 6-hydroxyhexyl, 2-methyl-3-phenyl-3-hydroxypropyl, 2-(4-methoxyphenyl)-2-hydroxyethyl, 2-(3-ethoxyphenyl)- 2-hydroxyethyl, 4-hydroxy-4-(3,4-dimethoxyphenyl)butyl, 3-methoxybenzyl, 4-methoxybenzyl, 2,4-diethoxybenzyl, 2,3-dimethoxybenzyl, 2,4-dimethoxybenzyl, 2,6-dimethoxybenzyl, 4-benzyloxybenzyl, 2-(3-benzyloxyphenyl)ethyl, 1-(2-benzyloxyphenyl)ethyl, 3-[2-( 2-phenylethoxy)phenyl]propyl, 4-[3-(3-phenylpropoxy)phenyl] butyl, 1,1-dimethyl-2-[4-(4-phenylbutoxy)phenyl]ethyl, 5-[2-(5-phenylpentyloxy)phenyl]pentyl, 6-[3-(6-phenylhexyloxy)phenyl] hexyl, 2-(4-benzyloxyphenyl)-2-hydroxyethyl, 2-[3-(2-phenylethoxy)phenyl]-2-hydroxyethyl, 4-hydroxy-4-(3,4-dibenzyloxyphenyl)butyl, 2-hydroxybenzyl, 2-(3-hydroxyphenyl)ethyl, 1-(4-hydroxyphenyl)ethyl, 3-(2-hydroxyphenyl)propyl, 4-(3-hydroxyphenyl)butyl, 5-(2-hydroxyphenyl)pentyl, 6-(3-hydroxyphenyl)hexyl, 3,4-dihydroxybenzyl, 3,4,5-trihydroxybenzyl, 2-(4-hydroxyphenyl)-2-hydroxyethyl, 4-hydroxy-4-( 2,3-dihydroxyphenyl)butyl, 3,5-dimethoxy-4-benzyloxybenzyl, 3,5-dimethoxy-4-hydroxybenzyl, 3,5-di-tert-butoxy- 4-hydroxybenzyl, 2-methylbenzyl, 2-(3-methylphenyl)ethyl, 1-(4-methylphenyl)ethyl, 3-(2-ethylphenyl)propyl, 4-(3-ethylphenyl)butyl, 1,1-dimethyl-2-( 4-ethylphenyl)ethyl, 5-(4-isopropylphenyl)pentyl, 6-(4-hexylphenyl)hexyl, 3,4-dimethylbenzyl, 3,4,5-trimethylbenzyl, 2,5-dimethylbenzyl, 2-(4-methylphenyl)-2-hydroxyethyl, 2-(3-ethylphenyl)-2-hydroxyethyl, 4-hydroxy- 4-(3,4-dimethylphenyl)ethyl, 2-chlorobenzyl, 2-( 3-chlorophenyl)ethyl, 2-fluorobenzyl, 1-(4-chlorophenyl)ethyl, 3-(2-fluorophenyl)propyl, 4-(3-fluorophenyl)butyl, 5-(4-fluorophenyl)pentyl, 1,1-dimethyl- 2-(2-bromophenyl)ethyl, 6- (3-bromophenyl ) hexyl, 4-bromobenzyl, 2-(2-iodophenyl)ethyl, 1-(3-iodophenyl)ethyl, 3-(4-iodophenyl)propyl, 3,4-dichlorobenzyl, 3,5-dichlorobenzyl, 2,6-dichlorobenzyl, 2,3-dichlorobenzyl, 2,4-dichlorobenzyl, 3,4-difluorobenzyl, 3,5-dibromobenzyl, 3,4,5-trichlorobenzyl and 2-methoxy-3-chlorobenzyl groups and the like.

The lower alkoxycarbonyl group means a straight chain or branched chain alkoxy group having 1 to 6 carbon atoms, there can be exemplified methoxycarbonyl, ethoxycarbonyl, propoxy-carbonyl, isopropoxycarbonyl, butoxycarbonyl, tert-butoxy-carbonyl, pentyloxycarbonyl and hexyloxycarbonyl groups and the like.

The 2,3-dihydroindenyl group which may have 1 to 5 substituents selected from the group consisting of a hydroxy group and a lower alkyl group means, a 2,3-dihydroindenyl group which may have 1 to 5 substituents selected from the group consisting of a hydroxy group and a straight chain or branched chain alkyl group having 1 to 6 carbon atoms, there can be exemplified 2,3-dihydroindenyl, 2,2,4,6-tetramethyl-7-hydroxy-2,3-dihydroindenyl, 2,4-dimethyl-2,3-dihydroindenyl, 6-hydroxy- 2,3-dihydroindenyl, 7-hydroxy-2,3-dihydroindenyl, 4-methyl-7-hydroxy-2,7-dihydroindenyl, 4-methyl- 2,3-dihydroindenyl, 6-ethyl-2,3-dihydroindenyl, 4-propyl-2,3-dihydroindenyl, 6-tert-butyl-2,3-dihydroindenyl, 4-pentyl-2,3-dihydroindenyl, 6-hexyl-2,3-dihydroindenyl, 2,2,4-trimethyl-2,3-dihydroindenyl and 2,2,4-trimethyl-7-hydroxy-2,3-dihydroindenyl groups and the like.

As to the 5- or 6-membered saturated heterocyclic group formed by combining the nitrogen atom to which $R^4$ and $R^5$ are directly bonded thereto, together with or without other nitrogen atom, oxygen atom or sulfur atoms, there can be exemplified piperazinyl, pyrrolidinyl, morpholinyl, piperidinyl and thiomorpholinyl groups and the like.

The heterocyclic group which may have, as the substituents, an oxo group, a lower alkoxycarbonyl group, a pyridyl group, a pyrazinylcarbonyl group which may have, on the pyrazine ring, 1 to 4 substituents selected from the group consisting of an oxo group and a lower alkyl group, or a phenyl group which may have, on the phenyl ring, a lower alkoxy group as the substituents, means a heterocyclic group which may have, as the substituents, an oxo group, a straight chain or branched chain alkoxycarbonyl group having 1 to 6 carbon atoms, a pyridyl group, a pyrazinylcarbonyl group which may have, on the pyrazine ring, 1 to 4 substituents selected from the groups consisting of an oxo group and a straight chain or branched chain alkyl group having 1 to 6 carbon atoms, or a phenyl group which may have, on the phenyl ring, 1 to 3 straight chain or branched chain alkoxy groups having 1 to 6 carbon atoms, there can be exemplified, 4-ethoxycarbonylpiperazinyl, 4-(3-methoxyphenyl] piperazinyl, 4-(2-pyridyl)piperazinyl, 1-oxothiomorpholino, 1,1-dioxothiomorpholino, 4-[2,4-dioxo- 3-isobutyl-5-ethylpyrazin-6-yl]piperazinyl, 2-oxopyrrolidinyl, 4-(2,4-dimethoxyphenyl)piperidinyl, 3-oxopiperidinyl, 4-(4-pyridyl)piperidinyl, 4-methoxycarbonylpiperidinyl, 3-oxomorpholinyl, 3-(2,3,4-trimethoxyphenyl)morpholinyl, 2-(3-pyridyl)morpholinyl, 3-ethoxycarbonylmorpholinyl, 3-(2-pyridyl)thiomorpholinyl, 2-ethoxycarbonylthiomorpholinyl and 3-(4-ethoxyphenyl)thiomorpholinyl groups and the like.

The pyrazinylcarbonyl group which may have, on the pyrazine ring, 1 to 4 substituents selected from the group consisting of an oxo group and a lower alkyl group means, a pyrazinylcarbonyl group which may have, on the pyrazine ring, 1 to 4 substituents selected from the group consisting of an oxo group and a straight chain or branched chain alkyl group having 1 to 6 carbon atoms, there can be exemplified pyrazinylcarbonyl, 2-oxopyrazinylcarbonyl, 2,4-dioxopyrazinylcarbonyl, 2-oxo-3-methylpyrazinylcarbonyl, 2-oxo-3-ethylpyrazinylcarbonyl, 3-propylpyrazinylcarbonyl, 3-isobutyl-5-ethylpyrazinylcarbonyl, 3-isobutyl-5-pentylpyrazinylcarbonyl, 3-isobutyl- 5-hexylpyrazinylcarbonyl, 2,4-dioxo-3-isobutyl- 4-ethylpyrazinylcarbonyl and 2,4-dioxo-3-isobutyl-4-ethylpyrazinylcarbonyl groups and the like.

The phenyl group which may have, on the phenyl ring, 1–3 substituents selected from the group consisting of a lower alkoxy group, a lower alkyl group and a lower alkanoyl group means, a phenyl group which may have, on the phenyl ring, the substituent selected from the group consisting of a straight chain or branched chain alkoxy group having 1 to 6 carbon atoms, a straight chain or branched chain alkyl group having 1 to 6 carbon atoms and a straight chain or branched chain alkanoyl group having 1 to 6 carbon atoms, there can be exemplified phenyl, 2-methoxyphenyl, 3-methoxyphenyl, 4-methoxyphenyl, 2-ethoxyphenyl, 3-ethoxyphenyl, 4-ethoxyphenyl, 3-isopropoxyphenyl, 4-butoxyphenyl, 2-pentyloxyphenyl, 3-hexyloxyphenyl, 3,4-dimethoxyphenyl, 2,5-dimethoxyphenyl, 3,4,5-trimethoxyphenyl, 2,5-dimethylphenyl, 2-methylphenyl, 3-methylphenyl, 4-methylphenyl, 2-ethylphenyl, 3-ethylphenyl, 4-ethylphenyl, 3-isopropylphenyl, 3-hexylphenyl, 3,4-dimethylphenyl, 3,4,5-trimethylphenyl, 2-formylphenyl, 4-acetylphenyl, 3-propionyl- phenyl, 2-butyrylphenyl, 3-isobutyrylphenyl, 4-gentanoylphenyl, 2-tert-butylcarbonylphenyl, 3-hexanoylphenyl and 2-methoxy-3-methylphenyl groups and the like.

The saturated or unsaturated 5- to 10-membered monocyclic or bicyclic heterocyclic residual group having 1 to 2 hetero atoms selected from the group consisting of a nitrogen atom, an oxygen atom and a sulfur atom, there can be exemplified pyrrolidinyl, piperidinyl, piperazinyl, morpholino, pyridyl, thienyl, quinolinyl, 1,4-dihydroquinolyl, benzothizolyl, pyrazinyl, pyrimidyl, pyridazinyl, pyrrolyl, carbostyrilyl, 3,4-dihydrocarbostyrilyl, 1,2,3,4-tetrahydroquinolyl, indolyl, isoindolyl, indonilinyl, benzimidazolyl, benzoxazolyl, imidazolidinyl, isoquinolyl, quinazolidinyl, quinoxalinyl, cinnolinyl, phthalazinyl, chromanyl, isoindolinyl, isochromanyl, pyrazolyl, imidazolynyl, pyrrazolidinyl, benzofuryl, benzothienyl, 4H-chromenyl, 1H-indazolyl, thienyl, isoindolingl, 2-imidazolinyl, 2-pyrrolinyl, furyl, oxazolyl, isooxazolyl, thiazolyl, isothiazolyl, pyranyl, pyrazolidinyl, 2-pyrrazolinyl, quinuclidinyl, 1,4-benzoxazinyl, 3,4-dihydro-2H-1,4-benzoxazinyl, 3,4-di-hydro- 2H-1,4-benzothiazinyl, 1,4-benzothiazinyl, 1,2,3,4-tetrahydroquinoxalinyl, 1,3-dithia-2,4-dihydronaphthalenyl and 1,4-dithianaphthalenyl groups and the like.

The heterocyclic group in which a lower alkoxy group or an oxo group is substituted, means a heterocyclic group having 1 to 3 straight chain or branched chain alkoxy groups or oxo groups as the substituents, there can be exemplified 4-oxo-1,4-dihydroquinolyl, 1-oxopyridyl, 2-oxopyridyl, 6-methoxybenzothiazolyl, 3-oxo- 3,4-dihydro-2H-1,4-benzothiazinyl, 2-methoxybenzothiazolyl, 3-oxo-3,4-dihydro-2H-1,4-benzoxazinyl, 2-oxobenzoimidazolyl, 2-oxobenzothiazolyl, 2-oxobenzoxazolyl, 3,4-dimethoxyquinolyl, 4-oxopyridyl, 2-ethoxybenzoxazolyl, 2-propoxybenzimidazolyl, 2-butoxybenzothiazolyl, 6-pentylcarbostyrilyl, 7-hexyloxycarbostyrilyl, 4-methoxypyrazolyl, 2-methoxypyridyl, 4-methoxy-2-oxopyridyl, 2-ethoxypyrrolyl, 5-methoxyindolyl, 5-ethoxy-1H-indanyl, 6-methoxybenzimidazolyl, 6,7,8-trimethoxyquinolyl, 3-methoxyfuryl, 2-methoxythienyl and 2-oxoindolyl groups and the like.

The saturated or unsaturated 5- to 10-membered monocyciic or bicyclic heterocyclic-substituted lower alkyl group, in which the heterocyclic moiety having 1 to 2 hetero atoms selected from the group consisting of a nitrogen atom, an oxygen atom and a sulfur atom, means a heterocyclic-substituted alkyl group in which the alkyl moiety is a straight chain or branched chain alkyl group having 1 to 6 carbon atoms, there can be exemplified pyrrolidinylmethyl, 2-piperidinylethyl, 3-piperazinylpropyl, 4-morpholinobutyl, (3-pyridyl)methyl, (2-thienyl)methyl, 5-(6-quinolyl)pentyl, 6-(1,4-dihydro- 2-quinolyl)hexyl, (2-benzothiazolyl)methyl, 2-(3-pyrazinyl)ethyl, 1-(2-pyrimidyl)ethyl, 3-(3-pyridazinyl)propyl, 4-(2-pyrrolyl)butyl, 5-(3-carbostyrilyl)gentyl, 6-(3,4-dihydrocarbostyril-6-yl)hexyl, (1,2,3,4-tetra-hydroquinolyl- 8-yl)methyl, (3-indolyl)methyl, 2-(3-indolyl)ethyl, (4-isoindolyl)methyl, 2-(3-indonylyl)ethyl, (2-benzimidazolyl)methyl, 3-(5-benzoxazolyl)propyl, 4-(4-imidazolidinyl)buty, 5-(1-isoquinolyl)gentyl, 6-(7-quinazolidinylphexyl, (8-quinoxalinyl)methyl, 1-(4-cinnolinyl)ethyl, 3-(5-phthalazinyl)propyl, 4-(6-chromanyl)butyl, 5-(4-isoindolinyl)pentyl, 6-(7-isochromanyl)hexyl, (3-pyrazolyl)methyl, 2-(2-imidazolyl)ethyl, 3-(3-pyrazolidinyl)propyl, 4-(6-benzofuryl)butyl, 5-(5-benzothienyl)pentyl, [6-(4H-chromenyl]methyl, (5-1-H-indazolyl)methyl, thienylmethyl, 1-(5-isoindolinyl)ethyl, 3-(2-imidazolinyl)propyl, 4-(2-pyrrolinyl)butyl, (2-furyl)methyl, 5-(4-oxazolyl)pentyl, 6-(3-isoxazolyl)hexyl, (2-thiazolyl)methyl, 2-(3-isothiazolyl)ethyl, (2-pyranyl)methyl, 3-(3-pyrazolidinyl)propyl, 4-(2-pyrazolidinyl)butyl, 5-(2-quinuclidinyl)pentyl, (6-1,4-benzoxadinyl)-methyl, (3,4-dihydro-2H-1,4-benzoxazin-2-yl)methl, (3,4-dihydro-2H-1,4-benzoxazin-2-yl)methyl, 1,4-benzothiazin-5-yl)methyl, (1,2,3,4-tetrahydroquinoxalinyl-6-yl)methyl, (1,3-dithia-2,4-dihydronaphthalen- 6-yl)methyl and (1,4-dithianaphthalen-7-yl)methyl groups and the like.

The heterocyclic-substituted lower alkyl group in which the heterocyclic moiety has, as the substituents, an oxo group or a lower alkoxycarbonyl group, further the lower alkyl moiety may have a carboxy group, a benzothiazolylaminocarbonyl group or a lower alkoxycarbonyl group as the substituent means a heterocyclic-substituted alkyl group in which the heterocyclic moiety having, as the substituents, an oxo group or a straight chain or branched chain alkoxycarbonyl group having 1 to 6 carbon atoms, further the lower alkyl moiety is a straight chain or branched chain alkyl group having 1 to 6 carbon atoms, which may have a carboxy group, a benzothiazolylaminocarbonyl group or a straight chain or branched chain alkoxycarbonyl group having 1 to 6 carbon atoms, there can be exemplified 2-(2-oxoindol-3-yl)ethyl, 1-(1-methoxycarbonyl- 3-indolnyl)ethyl, (1-tert-butoxycarbonyl-3-indolyl)methyl, 2-(1-ethoxycarbonyl-3-indolyl)ethyl, (4-oxo-1,4-dihydroquinolin-2-yl)methyl, 2- (1-oxo-2-pyridyl)ethyl, 1-(2-oxo-4-pyridyl)ethyl, 3- (3-oxo-3,4-dihydro- 2H-1,4-benzothiazin-5-yl)propyl, 4-(3-oxo-3,4-dihydro- 2H-1,4-benzoxadin-6-yl)butyl, 5-(2-oxo-4-benzimidazolyl)pentyl, 6-(2-oxo-6-benzothiazolyl)hexyl, (2-oxo-5-benzoxazolyl)methyl, 2-(4-oxo-2-pyridyl)ethyl, (2-oxo-3-pyridyl)methyl, 1-methoxycarbonyl-2-(3-indolyl)ethyl, 1-ethoxycarbonyl-l-(3-indolyl)methyl, 1-[(2benzothiazolyl)aminocarbonyl] -1-(3-indolyl)methyl, 1-carboxyl- 2-(3-indolyl)ethyl and 1-carboxyl-l-(3-indolyl)methyl groups and the like.

The phenyl-lower alkyl group, means a phenylalkyl group in which the alkyl moiety is a straight chain or branched chain alkyl group having 1 to 6 carbon atoms, there can be exemplified benzyl, 2-phenylethyl, 1-phenylethyl, 3-phenylpropyl, 4-phenylbutyl, 1,1-dimethyl-2-phenylethyl, 5-phenylpentyl, 6-phenylhexyl and 2-methyl-3-phenylpropyl groups and the like.

The indolyl-lower alkyl group means a indolylalkyl group in which the alkyl moiety is a straight chain or branched chain alkyl groups having 1 to 6 carbon atoms, there can be exemplified (3-indolyl)methyl, 2-(2-indolyl)ethyl, 1-(4-indolyl)ethyl, 3-(5-indolyl)propyl, 4-(6-indolyl)butyl, 1,1-dimethyl-2-(7-indolyl)ethyl, 5-(2-indolyl)pentyl, 6-(3-indolyl)hexyl and 2-methyl-3-(3-indolyl)propyl groups.

The lower alkenyl group means a straight chain or branched chain alkenyl group having 2 to 6 carbon atoms, there can be exemplified vinyl, allyl, 2-butenyl, 3-butenyl, 1-methylallyl, 2-pentenyl and 2-hexenyl groups and the like.

The phenoxy-lower alkyl group which may have, on the phenyl ring, 1 to 3 lower alkoxy groups as the substituents means a phenoxyalkyl group which may have, on the phenyl ring, to 3 straight chain or branched chain alkoxy groups having 1 to 6 carbon atoms as the substituents, further the alkyl moiety of the phenoxyalkyl group is a straight chain or branched chain alkyl group having 1 to 6 carbon atoms, there can be exemplified phenoxymethyl, 2-phenoxyethyl, 1-phenoxyethyl, 3-phenoxypropyl, 4-phenoxybutyl, 1,1-dimethyl-2-phenoxyethyl, 5-phenoxypentyl, 6-phenoxyhexyl, 2-methyl-3-phenoxypropyl, 2-(4-methoxyphenoxy)ethyl, 1-(3-methoxyphenoxy)ethyl, 2-methoxybenzyloxy, 3-(2-ethoxyphenoxy)propyl, 4-(3-ethoxyphenoxy)butyl, 1,1-dimethyl-2-(4-ethoxyphenoxy)ethyl, 5-(4-isopropoxyphenoxy)pentyl, 6-( 4-hexyloxyphenoxy)hexyl, 3,4-dimethoxybenzyloxy, 3,4,5-trimethoxybenzyloxy and 2,5-dimethoxybenzyloxy groups and the like.

The halogen atom includes a fluorine atom, a chlorine atom, a bromine atom and iodine atom.

The lower alkanoyl group means a straight chain or branched chain alkanoyl group having 1 to 6 carbon atoms, there can be exemplified formyl, acetyl, propionyl, butyryl, isobutyryl, pentanoyl, tert-butylcarbonyl and hexanoyl groups and the like.

The benzoyl group which may have, on the phenyl ring, 1 to 3 substituents selected from the group consisting of a lower alkoxy group and a hydroxy group, means a benzoyl group which may have, on the phenyl ring, 1 to 3 substituents selected from the group consisting of a straight chain or branched chain alkoxy group having 1 to 6 carbon atoms and a hydroxy group, there can be exemplified benzoyl, 2-methoxybenzoyl, 3-methoxybenzoyl, 4-methoxybenzoyl, 2-ethoxybenzoyl, 3-ethoxybenzoyl, 4-ethoxybenzoyl, 3-isopropoxybenzoyl, 4-hexyloxy-benzoyl, 3,4-dimethoxybenzoyl, 2,4-dimethoxybenzoyl, 3,4,5-trimethoxybenzoyl, 2-hydroxybenzoyl, 3-hydroxybenzoyl, 4-hydroxybenzoyl, 2,3-dihydroxybenzoyl, 3,4-dihydroxybenzoyl, 3,5-dihydroxybenzoyl, 3,4,5-trihydroxybenzoyl and 3,5-dimethoxy-4-hydroxybenzoyl groups and the like.

The benzoyl group having, on the phenyl ring, lower alkylenedioxy groups as the substituents, means a benzoyl group having, on the phenyl ring, straight chain or branched chain alkylenedioxy groups having 1 to 4 carbon atoms, there can be exemplified 3,4-methylenedioxybenzoyl, 2,3-methyledioxybenzoyl, 2,3-ethylenedioxybenzoyl, 3,4-trimethylenedioxybenzoyl and 3,4-tetramethylenedioxybenzoyl groups and the like.

The phenyl-lower alkyl group which may have, on the phenyl ring, 1 to 3 substituents selected from the group consisting of a lower alkoxy group and a halogen atom, means a phenyalkyl group which may have, on the phenyl ring, 1 to 3 substituents selected from the group consisting of straight chain or branched chain alkoxy group having 1 to 6 carbon atoms and halogen atoms, further the alkyl moiety of the phenylalkyl group is a straight chain or branched chain alkyl group having 1 to 6 carbon atoms, there can be exemplified, in addition to the above-mentioned phenyl-lower alkyl group, 2-(3-methoxyphenyl)ethyl, 1-(4-methoxyphenyl)ethyl, 2-methoxybenzyl, 3-methoxybenzyl, 3-(2-ethoxyphenyl)propyl, 4-(3-ethoxyphenyl)butyl, 1,1-dimethyl- 2-(4-ethoxyphenyl)ethyl, 5-(4-isopropoxyphenyl)pentyl, 6-(4-hexyloxyphenyl)hexyl, 3,4-dimethoxybenzyl, 2,4-dimethoxybenzyl, 3,4,5-trimethoxybenzyl, 2-chlorobenzyl, 2-(3-chlorophenyl)ethyl, 1-(4-chlorophenyl)ethyl, 3-(2-fluorophenyl)propyl, 4-(3-fluorophenyl)butyl, 5-(4-fluorophenyl)pentyl, 1,1-dimethyl-2-( 2-bromophenyl)ethyl, 6-(3-bromophenyl)hexyl, 4-bromobenzyl, 2-(2-iodophenyl)ethyl, 1-(3-iodophenyl)ethyl, 3-(4-iodophenyl)propyl, 3,4-dichlorobenzyl, 3,5-dichlorobenzyl, 2,6-dichlorobenzyl, 2,3-dichlorobenzyl, 2,4-dichlorobenzyl, 3,4-difluorobenzyl, 3,5-dibromobenzyl, 3,4,5-trichlorobenzyl and 2-methoxy-3-chlorobenzyl groups and the like.

The phenyl-lower alkenylcarbonyl group which may have, on the phenyl ring, 1 to 3 substituents selected from the group consisting of a hydroxy group and a lower alkoxy group, means a straight chain or branched chain alkenylcarbonyl group having 3 to 6 carbon atoms, having a phenyl group which may have 1 to 3 substituents selected from the group consisting of a hydroxy group and a straight chain or branched chain alkoxy group having 1 to 6 carbon atoms, there can be exemplified, cinnamoyl, 4-phenyl-3-butenoyl, 4-phenyl- 2-butenoyl, 5-phenyl-4-gentenoyl, 5-phenyl-3-pentenoyl, 5-phenyl-2-gentenoyl, 6-phenyl-5-hexenoyl, 6-phenyl-4-hexenoyl, 6-phenyl-3-hexenoyl, 6-phenyl-2-hexenoyl, 2-methyl-4-phenyl-3-butenyl, 2-methylcinnamoyl, 1-methylcinnamoyl, 2-, 3- or 4-methoxycinnamoyl, 4-ethoxyphenyl- 3-butenoyl, 4-(3-propoxyphenyl)-2-butenoyl, 5-(4-butoxyphenyl)-4-gentenoyl, 6-(2-pentyloxyphenyl)-5-hexenoyl, 2-methyl-(3-hexyoxly)cinnamoyl, 1-methyl-(3-hydroxy)cinnamoyl, 2-, 3- or 4-hydroxycinnamoyl, 3,5-dihydroxycinnamoyl, 2,6-dihydroxycinnamoyl, 3,4,5-trihydorxycinnamoyl, 4-hydroxyphenyl-3-butenoyl, 5-(2-hydroxyphenyl)-4-pentenoyl, 6-(3-hydroxyphenyl)-5-hexenoyl, 3,4-dimethoxycinnamoyl, 3,4,5-trimethoxycinnamoyl and 3-methoxy-4-hydroxycinnamoyl groups, and the like.

The phenyl-lower alkyl group which may have, on the phenyl ring, 1 to 3 substituents selected from the group consisting of a lower alkoxy group, a phenyl-lower alkoxy group, a lower alkyl group and a hydroxy group, means a phenyl alkyl group in which the alkyl moiety thereof is a straight chain or branched chain alkyl group having 1 to 6 carbon atoms, further which may have, on the phenyl ring, 1 to 3 substituents selected from the group consisting of a straight chain or branched chain alkoxy group having 1 to 6 carbon atoms, a phenylalkoxy group in which the alkoxy moiety is a straight chain or branched chain alkoxy group having 1 to 6 carbon atoms, a hydroxy group and a straight chain or branched chain alkyl group having 1 to 6 carbon atoms, there can be exemplified benzyl, 2-phenylethyl, 1-phenylethyl, 3-phenylpropyl, 4-phenylbutyl, 1,1-dimethyl- 2-phenylethyl, 5-phenylpentyl, 6-phenylhexyl, 2-methyl-3-phenylpropyl, diphenylmethyl, 2,2-diphenylethyl, 2-(3-methoxyphenyl)ethyl, 1-(4-methoxyphenyl)ethyl, 2-methoxybenzyl, 3-(2-ethoxyphenyl)propyl, 4-(3-ethoxyphenyl)butyl, 1,1-dimethyl-2-(4-ethoxyphenyl)ethyl, 5-(4-isopropoxyphenyl)pentyl, 6-(4-hexyloxyphenyl)hexyl, 3,4-dimethoxybenzyl, 3,4,5-trimethoxybenzyl, 2,5-dimethoxybenzyl, 2,4-diethoxybenzyl, 2,3-dimethoxybenzyl, 2,4-dimethoxybenzyl, 4-benzyloxybenzyl, 2,6-dimethoxybenzyl, 2-(3-benzyloxyphenyl)ethyl, 1-(2-benzyloxyphenyl)ethyl, 3-[2-(2-phenylethoxy)phenyl]propyl, 4-[3-(3-phenylpropoxy)phenyl]butyl, 1,1-dimethyl- 2-[4-(4-phenylbutoxy)phenyl]ethyl, 5-[2-(5-phenylpentyloxy)phenyl] pentyl 6-[3-(6-phenylhexyloxy)phenyl] hexyl, 2-(4-benzyloxyphenyl)-2-hydroxyethyl, 2-[ 3-(2-phenylethoxy)phenyl]-2-hydroxyethyl, 4-hydroxy-4-( 3,4-dibenzyloxyphenyl)butyl, 2-hydroxybenzyl, 2-(3-hydroxyphenyl)ethyl, 1-(4-hydroxyphenyl)ethyl, 3-(2-hydroxyphenyl)propyl, 4-(3-hydroxyphenyl)butyl, 5-(2-hydroxyphenyl)pentyl, 6-(3-hydroxyphenyl)hexyl, 3,4-dihydroxybenzyl, 3,4,5-trihydroxybenzyl, 2-(4-hydroxyphenyl)- 2-hydroxyethyl, 4-hydroxy-4-(2,3-dihydroxyphenyl)butyl, 3,5-dimethoxy-4-benzyloxybenzyl, 1,5-dimethoxy-4-hydroxybenzyl, 3,5-di-tert-butoxy-4-hydroxybenzyl, 2-methylbenzyl, 2-(3-methylphenyl)ethyl, -(4-methylphenyl)ethyl, 3-(2-ethylphenyl)propyl, 4-(3-ethylphenyl)butyl, 1,1-dimethyl-2-(4-ethylphenyl)ethyl, -(4-isopropylphenyl)pentyl, 6-(4-hexylphenyl)hexyl, 3,4-dimethylbenzyl and 3,4,5-trimethylbenzyl groups, and the like.

Pyrazine derivatives and salts thereof of the present invention represented by the formula (1) can be prepared by various processes, and preferable examples of the processes are as follows:

Reaction scheme-1

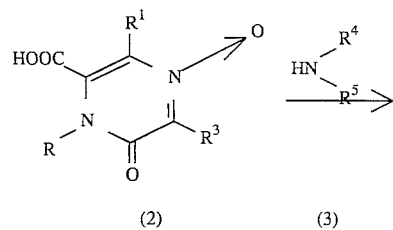

(2)            (3)

-continued
Reaction scheme-1

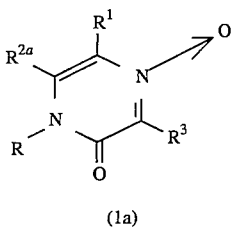

(1a)

wherein R, R$^1$, R$^3$, R$^4$ and R$^5$ are the same as defined above; and R$^{2a}$ is a group of the formula

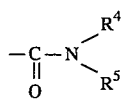

(wherein R$^4$ and R$^5$ are the same as defined above).

The above-mentioned reaction of a compound (2) with a compound (3) can be carried out by methods commonly used in amide-bond formation reactions. As to the amide-bond formation reactions, there are exemplified various methods: such as (a) a mixed acid anhydride method, that is a method by reacting a carboxylic acid (2) with a halocarboxylic acid alkyl ester to obtain a mixed acid anhydride, then reacting said mixed acid anhydride with an amine (3);

(b) an activated ester method, that is a method by converting a carboxylic acid (2) into an activated ester for example, p-nitrophenyl ester, N-hydroxysuccinimide ester, 1-hydroxybenzotriazole ester or the like, then by reacting said activated ester with an amine (3);

(c) a carbodiimide method, that is a method by condensing a carboxylic acid (2) with an amine (3) in the presence of an activating agent for example dicyclohexyl-carbodiimide, carbonyldiimidazole or the like;

(d) other methods, for example, a method by converting a carboxylic acid (2) into a carboxylic acid anhydride by using a dehydrating agent such as acetic anhydride, then reacting said carboxylic acid anhydride with an amine (3); or a method by reacting a lower alcohol ester of carboxylic acid (2) with an amine (3) under a high pressure and at an elevated temperature; or a method by converting a carboxylic acid (2) into a carboxylic acid halide, then such carboxylic acid halide is reacted with an amine (3); or a method by activating a carboxylic acid (2) with a phosphorus compound such as triphenylphosphine, diethylchlorophosphate or the like, then reacting said activated compound with an amine (3); or a method by converting a carboxylic acid (2) into an N-carboxyamino acid anhydride by using phosgen or trichloromethyl chloroformate or the like, then said N-carboxyamino acid anhydride is reacted with an amine (3). Further, the above-mentioned reaction of a compound (2) with a compound (3) can be carried out by a method of activating a carboxylic acid (2) by using an acetylene compound such as trimethylsilylethoxyacetylene or the like, then said activated compound is reacted with an amine (3).

The mixed acid anhydride used in the method (a) is mentioned above can be prepared by a conventional Schotten-Baumann reaction, and a compound (1a) is obtained by reacting said mixed acid anhydride, without being separated from the Schotten-Baumann reaction system, with an amine (3). The Schotten-Baumann reaction is generally carried out in the presence of a basic compound. As to the basic compound, any compound usually used in Schotten-Baumann reaction can also be used, for example, an organic basic compound such as triethylamine, trimethylamine, pyridine, dimethylaniline, N-methylmorpholine, 4-dimethylaminopyridine, 1,5-diazabicyclo[4.3.0]nonene-5 (DBN), 1,8-diazabicyclo [5.4.0]undecene-7 (DBU), 1,4-diazabicyclo[2.2.2]octane (DABCO) or the like; an inorganic basic compound such as potassium carbonate, sodium carbonate, potassium hydrogen carbonate, sodium hydrogen carbonate or the like can be exemplified. Said reaction is carried out at −20° to 100° C., preferably at 0° to 50° C, and for about 5 minutes to 10 hours, preferably for about 5 minutes to 2 hours. The reaction of the mixed acid anhydride thus obtained with an amine (3) is carried out at a temperature of about −20° to 150° C., preferably at 10° to 50° C., for about 5 minutes to 10 hours, preferably for about 5 minutes to 5 hours.

The reaction of the mixed acid anhydride method is generally carried out in the absence or presence of a solvent which is usually used in this type of mixed acid anhydride method, specifically, a halogenated hydrocarbon such as methylene chloride, chloroform or dichloroethane or the like; an aromatic hydrocarbon such as benzene, toluene, xylene or the like; an ether such as diethyl ether, dioxane, diisopropyl ether, tetrahydrofuran or dimethoxy ethane or the like; an ester such as methyl acetate or ethyl acetate or the like; an aprotic polar solvent such as 1,1,3,3-tetramethylurea, N,N-dimethylformamide, dimethyl sulfoxide, hexamethylphosphoryl triamide or the like; or a mixture of the above-mentioned solvents.

As to the alkyl ester of halocarboxylic acid to be used in preparation of the above-mentioned mixed acid anhydride, there can be exemplified methyl chloroformate, methyl bromoformate, ethyl chloroformate, ethyl bromoformate, isobutyl chloroformate or the like. The alkyl ester of halocarboxylic acid may be used generally at least in an equimolar quantity, preferably in 1 to 1.5 times molar quantities to one molar quantity of the amine (3). Further, the carboxylic acid (2) may be used generally at least in an equimolar quantity, preferably in 1 to 1.5 times molar quantity to one molar quantity of the amine (3).

The above-mentioned activated ester method (b) is carried out, for example in the case of using N-hydroxy-succiniimide ester, in the absence or presence of a suitable solvent which may not give any adverse effect to the reaction. In carrying out said reaction, a condensing agent such as dicyclohexylcarbodiimide, carbonyldiimidazole, 1-ethyl-3-(3'-dimethylaminopropyl)carbodiimide or the like may be added to the reaction system. As to the basic compound, any basic compound which can be used generally in the above-mentioned Schotten-Baumann reaction can also be used, in addition thereto, an alkali metal salt of a carboxylic acid, such as sodium acetate, sodium benzoate, sodium formate, potassium acetate, lithium benzoate, cesium acetate or the like; an alkali metal halide, such as potassium fluoride, cesium fluoride or the like can also be used. As to the solvent, there can be exemplified a halogenated hydrocarbon such as methylene chloride, chloroform, dichloroethane or the like; an aromatic hydrocarbon such as benzene, toluene, xylene or the like; an ether such as diethyl ether, dioxane, tetrahydrofuran, dimethoxy ethane or the like; an ester such as methyl acetate, ethyl acetate or the like; an aprotic polar solvent such as N,N-dimethylformamide, dimethyl sulfoxide, hexamethylphosphoryl triamide or the like; or a mixture of these solvents. The reaction can be carried out at 0° to 150° C., preferably at 10° to 100° C., and is completed in 5 to 30 hours. The amount of the amine (3) and of N-hydroxysuccinimide ester is generally at least in an equimolar quantity, preferably in an equimolar to 2 times molar quantities per molar quantity of the compound (2).

The compound (1a) can also be obtained by reacting an amine (3) with a carboxylic acid (2) in the presence of a condensing agent of phosphorus compound such as triphenylphosphine, triphenylphosphine-2,2'-dipyridyl disulfide, diethyl chlorophosphate, diphenylphosphinyl chloride, phenyl N-phenylphosphoramidochloridate, diethyl cyanophosphate, bis(2-oxo-3-oxazolidinyl)phosphinic chloride or the like. As to the basic compound to be used in this reaction, any basic compound widely known in the art can be used, for example basic compounds which can be used in the above-mentioned Schotten-Baumann reaction, further sodium hydroxide, potassium hydroxide can be exemplified. As to the solvent, in addition to the solvents used in the above-mentioned mixed acid anhydride method, pyridine, acetone, acetonitrile or the like or a mixture of these solvents can be exemplified.

The reaction is carried out, generally at −20° to 150° C., preferably at 0° to 100° C., and generally the reaction is completed in 5 minutes to 30 hours. The amounts of the condensing agent and the carboxylic acid (2) may be at least in an equimolar quantity, respectively, preferably 1 to 2 times molar quantity per molar quantity of the amine (3).

The compound (1a) can also obtained by reacting an amine (3) with a carboxylic acid (2) in the presence of a condensing agent. This reaction can be carried out in a suitable solvent, in the presence or absence of a catalyst. As to the solvent used in this reaction, a halogenated hydrocarbon such as dichloromethane, dichloroethane, chloroform, carbon tetrachloride or the like; acetonitrile, or dimethylformamide can be exemplified. As to the catalyst, an organic basic compound such as dimethylaminopyridine, 4-piperidinopyridine or the like; an organic salt such as pyridinium citrate or the like; camphorsulfonic acid, and mercury oxide can be exemplified. As to the condensing agent, an acetylene compound such as trimethylsilylethoxyacetylene or the like can be exemplified. The condensing agent may be used generally in an equimolar to 10 times molar quantities, preferably 2 to 6 times molar quantities per molar quantity of the amine (3). The carboxylic acid (2) may be used generally in at least an equimolar quantity, preferably an equimolar to 2 times molar quantities to molar quantity of the amine (3). The reaction is generally carried out at about 0° to 150° C., preferably at about room temperature to 100° C., and is completed in about 1 to 10 hours.

In carrying out the above-mentioned method (d), by reacting a carboxylic acid halide with an amine (3), the reaction is carried out in the presence of a dehydrohalogenating agent in a suitable solvent. As to the dehydrohalogenating agent, a common basic compound is used. As to the basic of compound, those of known widely in the art can be used, for example, other than basic compounds used in the Schotten-Baumann reaction, sodium hydroxide, potassium hydroxide, sodium hydride, potassium hydride and the like can be exemplified. As to the solvent, other than the solvents used in the above-mentioned mixed acid anhydride method, an alcohol such as methanol, ethanol, propanol, butanol, 3-methoxy-1-butanol, ethyl cellosolve, methyl cellosolve or the like; pyridine, acetone, acetonitrile or the like; and a mixture of these solvents can exemplified. The ratio of amounts of the amine (3) to that of carboxylic acid halide is not specifically restricted and can be selected from a wide range, and generally the latter may be used in at least an equimolar quantity, preferably in an equimolar to 5 times molar quantities to molar quantity of the fomer. The reaction is generally carried out at −20° to 180° C., preferably at about 0° to 150° C., and the reaction is generally completed in about 5 minutes to 30 hours.

In the above reaction, the carboxylic acid halide is prepared by reacting, for example a carboxylic acid (2) with a halogenating agent in the absence or presence of a solvent. As to the solvent used in this reaction, any solvent which does not give any adverse effect to the reaction may be used, for example, an aromatic hydrocarbon such as benzene, toluene, xylene or the like; a halogenated hydrocarbon such as chloroform, methylene chloride, carbon tetrachloride or the like; an ether such as dioxane, tetrahydrofuran, diethyl ether or the like; dimethylformamide and dimethyl sulfoxide can be exemplified. As to the halogenating agent, a common halogenating agent which changes the hydroxy group in the carboxy group to a halogen can be used, for example, thionyl chloride, phosphorus oxychloride, phosphorus oxybromide, phosphorus pentachloride, phosphorus pentabromide and the like can be exemplified. The ratio of amounts of the carboxylic acid (2) to the halogenating agent is not specifically restricted, and can be selected from a wide range, and in the case of carrying out the reaction in the absence of a solvent, generally the latter is used in a large excess amount to the former. While, in the case of carrying the reaction in the presence of a solvent, generally the latter is used in at least an equimolar quantity, preferably 2 to times of molar quantities is used to a molar quantity of the former. The reaction temperature (and the reaction time) is not specifically restricted, and generally, the reaction is carried out at about room temperature to 100° C., preferably at 50° to 80° C., and for about 30 minutes to 6 hours.

The starting compound (2) can be prepared by the Reaction scheme-2 as follows:

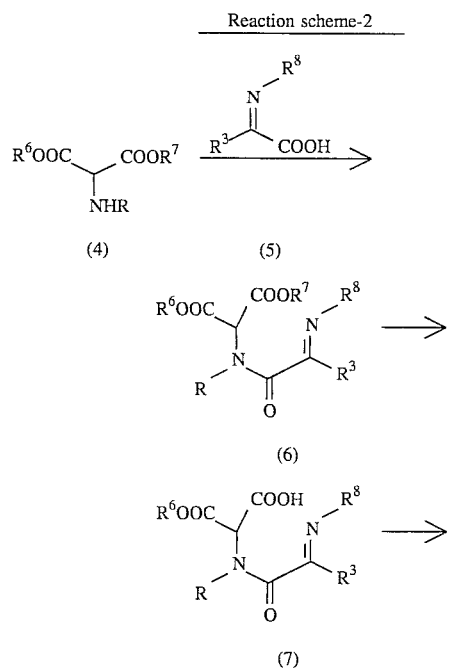

-continued
Reaction scheme-2

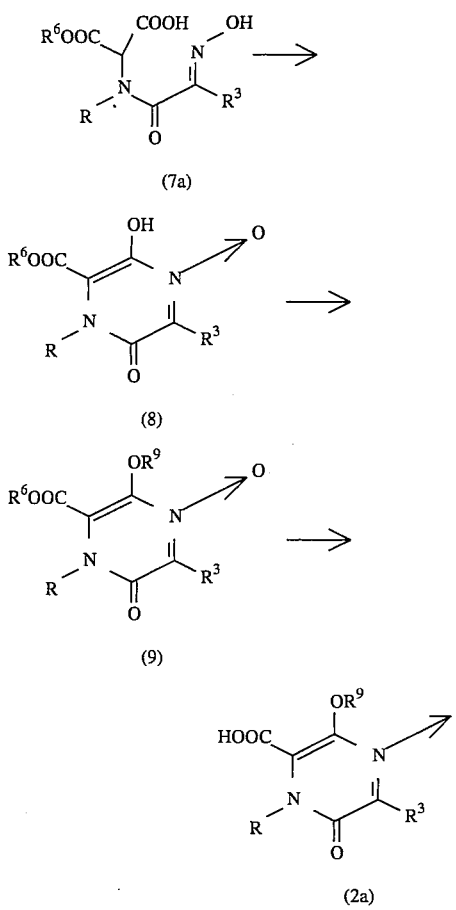

(wherein R and $R^3$ are the same as defined above; $R^6$ and $R^7$ are each a lower alkyl group; $R^8$ is a hydroxy group, a phenyl-lower alkoxy group which may have, on the phenyl ring, the substituents selected from the group consisting of a halogen atom, a lower alkyl group, a lower alkoxy group, a nitro group and an amino group, a tetrahydropyranyloxy group, a silyloxy group having 1 to substituents selected from the group consisting of a lower alkyl group and a phenyl group, or a lower alkoxysubstituted lower alkoxy group; $R^9$ is a lower alkyl group).

As to the phenyl-lower alkoxy group which may have, on the phenyl ring, the substituents selected from the group consisting of a halogen atom, a lower alkyl group, a lower alkoxy group, a nitro group and an amino group, there can be exemplified a phenyl-lower alkoxy group which may have, on the phenyl ring, 1 to 3 substituents selected from the group consisting of a halogen atom, a straight chain or branched chain alkyl group having 1 to 6 carbon atoms, a nitro group, an amino group, and a straight chain or branched chain alkoxy group having 1 to 6 carbon atoms, and the alkoxy moiety in the phenyl-lower alkoxy group is a straight chain or branched chain alkoxy group having 1 to 6 carbon atoms, such as benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy, 2-methyl-3-phenylpropoxy, 2-chlorobenzyloxy, 2-(3-chlorophenyl)ethoxy, 1-(4-chlorophenyl)ethoxy, 3-( 2-fluorophenyl)propoxy, 4-(3-fluorophenyl)butoxy, 1,1-dimethyl-2-(4-fluorophenyl)ethoxy, 5-(2-bromophenyl)pentyloxy, 6-(3-bromophenyl ) hexyloxy, 2-methyl-3-(4-bromophenyl ) propoxy, 3-iodobenzyloxy, 2-( 4-iodophenyl)ethoxy, 1- (3,5-dichlorophenyl) ethoxy, 2-(3,4-dichlorophenyl)ethoxy, 3-(2, 6-dichlorophenyl)propoxy, 4-(3,4-dichlorophenyl)butoxy, 1,1-dimethyl-2-(3,4-difluorophenyl)ethoxy, 5-(3,5-dibromophenyl)pentyloxy, 6-(3,4,5-trichlorophenyl)hexyloxy, 4-methylbenzyloxy, 2-(2-methylphenyl)ethoxy, 1-(3-methylphenyl)ethoxy, 3-(3ethylphenyl)propoxy, 4-(2-ethylphenyl)butoxy, 5-(4ethylphenyl)pentyloxy, 6-(3-isopropylphenyl)hexyloxy, 2-methyl- 3-(4-hexylphenyl)propoxy, 2-(3,4-dimethylphenyl)ethoxy, 2-(2,5-dimethylphenyl)ethoxy, 2-(3,4,5-trimethylphenyl)ethoxy, yl)ethoxy, 4-methoxybenzyloxy, 3,4-dimethoxybenzyloxy, 3,4,5-trimethoxybenzyloxy, 1-(3-methoxyphenyl)ethoxy, 2-(2-methoxyphenyl )ethoxy, 3-(2-ethoxyphenyl)propoxy, 4-(4-ethoxyphenyl )butoxy, 5-(3-ethoxyphenyl)pentyoxy, 6-(4-isopropoxyphenyl)hexyloxy, 1,1,-dimethyl-2-(4-hexyloxyphenyl)ethoxy, 2-methyl-3-( 3,4-dimethoxyphenyl)propoxy, 2-(3,4-dimethoxyphenyl)ethoxy, 2-(3,4-diethoxyphenyl)ethoxy, 2-(3,4,5-trimethoxyphenyl)ethoxy, 1-(2,5-dimethoxyphenyl)ethoxy, (2-chloro-4-methoxy)benzyloxy, 2-aminobenzyloxy, 1-(3-aminophenyl)ethoxy, 1-(4-aminophenyl)propoxy, 1-(2,3-diaminophenyl)butoxy, 1-(2,3,4-triaminophenyl)pentyloxy, 1-(2,4-diaminophenyl)hexyloxy, 2-nitrobenzyloxy, 1-(3-nitrophenyl)ethoxy, 1-(4-nitrophenyl)propoxy, 1-(2,4-dinitrophenyl)butoxy, 1-(2,4,6-trinitrophenyl)pentyloxy, 1-(2-chloro-4-nitrophenyl)hexyloxy, (3-methyl-4-amino)benzyloxy, trityloxy and diphenylmethoxy group. Among these phenyl-lower alkoxy groups, those having 1 to 3 unsubstituted or substituted phenyl groups at 1-position in the alkyl moiety, for example, benzyloxy, 1-phenylethoxy, 1-(4-chlorophenyl)ethoxy, 1-(3, 5-dichlorophenyl)ethoxy, 1-(3-methylphenyl)ethoxy, 1-(3-methoxyphenyl)ethoxy, 1-(2,5-dimethoxyphenyl)ethoxy, trityloxy and diphenylmethoxy groups are preferable.

As to the silyloxy group having 1 to 3 substituents selected from the group consisting of a lower alkyl group and a phenyl group, there can be exemplified silyloxy group having 1 to 3 substituents selected from the group consisting of a straight chain or branched chain alkyl group having 1 to 6 carbon atoms and a phenyl group, such as trimethylsilyloxy, triethylsilyloxy, tripropylsilyloxy, tributylsilyloxy, tert-tbutylsilyloxy, tert-butyldiphenylsilyloxy, tripentylsilyloxy, trihexylsilyloxy or dimethylethylsilyloxy group or the like.

As to the lower alkoxy-substituted lower alkoxy group, there can be exemplified an alkoxy-substituted alkoxy group in which the alkoxy moiety is a straight chain or branched chain alkoxy group having 1 to 6 carbon atoms, such as methoxymethoxy, 2-methoxyethoxy, 1-ethoxyethoxy, 3-propoxypropoxy, 4-butoxybutoxy, 5-pentyloxypentyloxy, 6-hexyloxyhexyloxy, 1,1-dimethyl- 2-methoxyethoxy and 2-methyl-3-methoxypropoxy groups and the like. Among these groups, specifically 1-lower alkoxy-substituted lower alkoxy group, such as methoxymethoxy, 1-ethoxyethoxy groups are preferable.

The reaction of a compound (4) with a compound (5) can be carried out under conditions similar to those employed in the reaction of a compound (2) with a compound (3) in the above-mentioned Reaction scheme-1.

The reaction of introducing a compound (6) to a compound (7) can be carried out in accordance with a conventional hydrolysis reaction. Said hydrolysis reaction can be carried out, specifically, in the presence of a mineral acid such as sulfuric acid, hydrochloric acid, nitric acid and the like, an organic acid such as acetic acid, aromatic sulfonic acid and the like, or in the presence of a basic compound such as sodium carbonate, potassium carbonate, sodium hydroxide, potassium hydroxide and barium hydroxide and the like, and in a solvent or mixed solvent thereof, for example water or an alcohol such as methanol, ethanol, isopropyl alcohol or the like, a ketone such as acetone, methylethyl ketone or the like, or an ether such as dioxane, ethylene glycol dimethyl ether or the like, or acetic acid. The hydrolysis reaction can be proceeded generally at about 0° to 200° C., preferably at room temperature to about at 150° C., and generally the reaction is completed in about 0.5 to 15 hours.

The reaction of introducing a compound (7) to a compound (7a) can be carried out by reducing a compound (7), when $R^8$ is a substituted or unsubstituted phenyl-lower alkoxy group. This reducing reaction can be carried out by a catalytic hydrogenation in a suitable solvent in the presence of a catalyst. As to the solvent to be used, there can be exemplified, water; acetic acid; an alcohol such as methanol, ethanol, isopropanol, and the like; a hydrocarbon such as hexane, cyclohexane or the like; an ether such as dioxane, tetrahydrofuran, diethyl ether, ethylene glycol dimethyl ether or the like; an ester such as ethyl acetate, methyl acetate or the like; an aprotic polar solvent such as dimethylformamide or the like; or a mixed solvent thereof. As to the catalyst to used, there can be exemplified palladium, palladium-black, palladiumcarbon, platinum, platinum oxide, copper chromite, and Raney nickel. Amount of the catalyst may be generally about 0.02 time of quantity to an equivalent quantity to one part of a compound (7). The reaction temperature is generally about 20° to 100° C., preferably about at 0° to 80° C., and hydrogen pressure may be generally about 1 to 10 atmospheric pressure, the reaction is generally completed in 0.5 to 20 hours.

Further, when $R^8$ is a tetrahydropyranyloxy group or a silyloxy group having 1 to 3 substituents selected from the group consisting of a lower alkyl group and a phenyl group, the reaction of introducing a compound (7) to a compound (7a) is carried out by hydrolyzing a compound (7). The hydrolysis reaction is carried out in a suitable solvent or without solvent in the presence of an acid. As to the solvent to be used in this hydrolysis, any solvent which may not give any adverse effect can be used, for example, water, a halogenated hydrocarbon such as dichloromethane, chloroform or the like; a lower alcohol such as methanol, ethanol, isopropanol or the like; a ketone such as acetone, methylethyl ketone or the like; an ether such as dioxane, tetrahydrofuran, ethylene glycol monomethyl ether, ethylene glycol dimethyl ether, or the like; an aliphatic fatty acid such as formic acid, acetic acid or the like; or a mixed solvent thereof. As to the acid to be used in this hydrolysis, a mineral acid such as hydrochloric acid, sulfuric acid, hydrobromic acid or the like; an organic acid such as formic acid, trifluoroacetic acid, acetic acid, an aromatic sulfonic acid can be exemplified. Amount of the acid to be used in this hydrolysis reaction is not specifically restricted, and can suitably be selected from a wide range, and generally, an equimolar to a large excess quantity, and preferably about 10 to 20 molar quantity can be used. The hydrolysis can be carried out at about 0° to 200° C., preferably the reaction can be proceeded at about room temperature to 150° C. and the reaction is generally completed in about 0.5 to 15 hours. Further, when $R^8$ is a silyloxy group having 1 to 3 substituents selected from the group consisting of a lower alkyl group and a phenyl group, the reaction may be carried out by using a fluorine compound such as tetra-n-butyl ammonum fluoride, hydrogen fluoride, cesium fluoride and the like, Further, when $R^8$ is a lower alkoxy-lower alkoxy group, the reaction of introducing a compound (7) to a compound (7a) can be carries out by treating a compound (7) in a mixture of a mineral acid such as hydrobromic acid, hydrochloric acid or an organic acid such as p-toluenesulfonic acid, together with a solvent such as water, methanol, ethanol, isopropanol or the like, under the temperature condition of about at 0° to 150° C., preferably at about room temperature to 120° C., or hydrolyzing a compound (7). In carrying out of the latter reaction of hydrolysis, the reaction is carried out in a suitable solvent, in the presence of an acid. As to the solvent to be used in this hydrolysis, water, a lower alcohol such as methanol, ethanol, isopropanol or the like; an ether such as dioxane, tetrahydrofuran or the like, a halogenated hydrocarbon such as dichloromethane, chloroform, carbon tetrachloride or the like; a polar solvent such as acetonitrile or the like, or a mixture of these solvents can be exemplified. As to the acid, a mineral acid such as hydrochloric acid, sulfuric acid, hydrobromic acid, an aliphatic patty acid, such as formic acid, acetic acid or the like: or a Lewis acid, boron trifluoride, aluminum chloride, boron tribromide or the like; an iodide such as sodium iodide, potassium iodide; or a mixture of the above-mentioned Lewis acid with an iodide can be exemplified. The reaction can be proceeded, generally at about 0° to 150° C., preferably at about room temperature to 100° C., and generally the reaction is completed in 0.5 to 1.5 hours.

The reaction of introducing a compound (7a) to a compound (8) can be carried out under the conditions as the same as employed in the reaction of a compound (2) with a compound (3) in the above-mentioned Reaction scheme-1.

The reaction of introducing a compound (8) to a compound (9) can be carried out in a suitable solvent, in the absence or presence of a catalyst, by reacting the above-mentioned formed product with an alkylating agent. As to the solvent used in this reaction, a lower alcohol such as methanol, ethanol, propyl alcohol or the like; an ether such as dioxane, tetrahydrofuran, diethyl ether, ethylene glycol monomethyl ether or the like; a halogenated hydrocarbon such as dichloromethane, chloroform, carbon tetrachloride or the like; or a mixed solvent thereof can be exemplified. Further as to the catalyst, a Lewis acid such as boron tribromide, boron trifluoroide-diethyl ether can be exemplified. As to the alkylating agent, in the case of using diazomethane, it may be used, generally 1 to 2 times of the molar quantity to per mole of the starting material, while in the case of using other alkylating agent, at least an equimolar quantity, preferably an equimolar quantity to 3 times of the molar quantity may be used. As to the alkylating agent, diazomethane, trimethylsilyldiazomethane, an alkyl halide such as methyl iodide or the like, a lower alkylsulfonic acid ester such as $FSO_3CH_3$, $CF_3SO_3CH_3$, $(CH_3)_2SO_4$ or the like; a lower alkyloxonium halide chelate such as $(CH_3)O\oplus BF_4\ominus$, $(C_2H_5)_3O\oplus BF_4\ominus$ or the like; a lower alkoxyoxonium halide chelate such as $(C_2H_5O)_3O\oplus BF_4\ominus$ or the like can be exemplified. The reaction can be carried out, generally at about −30° to 100° C. preferably at about −20° to 70° C., and the reaction is generally completed in 0.5 to 20 hours. The purity and stability of compound (8) can be increased by forming its salt with an organic amine such as DBU, DBN, diisopropylethylamine or the like, or with an alkali metal such as sodium, potassium or the like to form an alkali metal salt, so that such organic amine salt or alkali metal salt can advantageously be used to the next reaction steps.

Under the reaction condition for introducing a compound (8) to a compound (9), when R in the compound (8) is a hydrogen atom, then a compound (9) in which 1-position in the pyrazine ring is simultaneously alkylated as well the same compound having R as a lower alkyl group can also be obtained, such compound, such compounds can easily be separated from each other.

The hydrolysis reaction of a compound (9) can be carried out under the same condition as employed in the hydrolysis of the above-mentioned compound (6).

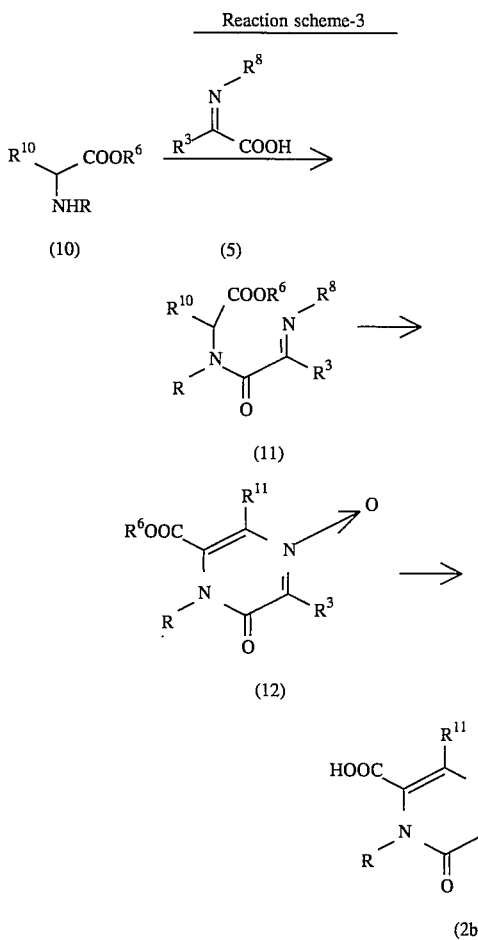

Reaction scheme-3

(wherein R, $R^3$, $R^6$ and $R^8$ are the same as defined above; $R^{10}$ is a lower alkanoyl group; and $R^{11}$ is a lower alkyl group).

As to the lower alkanoyl group, a straight chain or branched chain alkanoyl group having 1 to 6 carbon atoms, such as formyl, acetyl, propionyl, butyryl, isobutyryl, pentanoyl and hexanoyl groups can be exemplified.

The reaction of a compound (10) with a compound (5) is carried out under the same conditions as those employed in the reaction of a compound (2) with a compound (3) in the above-mentioned Reaction scheme-1.

The reaction of introducing a compound (11) to a compound (12) is carried out in a solvent or without solvent, in the presence of an acid. As to the solvent, those used in the reaction of an acid halide of carboxylic acid (3) with an amine (2) may also be used. As to the acid, a mineral acid such as hydrochloric acid, sulfuric acid, hydrobromic acid or the like; an organic acid such as formic acid, acetic acid, trifluoroacetic acid, trifloromethanesulfonic acid, an aromatic sulfonic acid such as p-toluenesulfonic acid, boron trifluoride-diethyl etherate or the like can be exemplified. The reaction is generally carried out at about 0° to 150° C., preferably at about room temperature to 100° C., and the reaction is generally completed in 1 hour to 10 days. Further, an alkylsilyl halide such as trimethylsilyl chloride may be added to this reaction system.

The hydrolysis reaction of a compound (12) is carried out under the same conditions as those employed in the hydrolysis of a compound (9) in the above-mentioned Reaction scheme-2.

In a compound (1), wherein $R^4$ is a saturated or unsaturated 5- to 10-membered monocyclic or bicyclic heterocyclic-substituted lower alkyl group (in which the heterocyclic moiety having 1 to 2 heteroatoms selected from the group consisting of a nitrogen atom, an oxygen atom and a sulfur atom, and the lower alkyl moiety may have a carboxy group, a benzothiazolylaminocarbonyl group or a lower alkoxycarbonyl group), then the corresponding compound (1) in which $R^4$ is a heterocyclic-substituted lower alkyl group, wherein the lower alkoxycarbonyl group bonded to the nitrogen atom in the heterocyclic ring is substituted by a hydrogen atom can be introduced by hydrolyzing the starting compound (1). Said hydrolysis reaction is carried out in a suitable solvent or without solvent, in the presence of an acid or a basic compound.

As to the solvent, any solvent which does not give any adverse effect to the reaction may be used, there can be exemplified, water; a halogenated hydrocarbon such as dichloromethane, chloroform or the like; a lower alcohol such as methanol, ethanol, isopropanol or the like; a ketone such as acetone, methylethyl ketone or the like; an ether such as dioxane tetrahydrofuran, ethylene glycol monomethyl ether, ethylene glycol dimethyl ether or the like; a fattyl acid such as formic acid; dimethylformamide or the like, or a mixed solvents thereof. As to the acid, a mineral acid such as hydrochloric acid, sulfuric acid, hydrobromic acid or the like; an organic acid such as formic acid, trifluoroacetic acid, acetic acid, an aromatic sulfonic acid or the like, and as to the basic compound such as sodium carbonate, potassium carbonate, a metal hydroxide such as sodium hydroxide, potassium hydroxide, calcium hydroxide or the like; a alkali metal alcoholate such as sodium methylate, sodium ethylate or the like may be exemplified. Amount of the acid or basic compound is not specifically restricted and can suitably be selected from a wide range, and generally an equimolar to a large excess quantity, preferably 1 to 2 molar quantity may be used to per molar quantity of the starting material. The reaction can be proceeded generally at about room temperature to 200° C., preferably at about room temperature to 150° C., and is completed in about 5 minute to 7 days.

In a compound (1), wherein $R^4$ is a substituted or unsubstituted saturated or unsaturated 5- to 10membered monocyclic or bicyclic heterocyclic-substituted lower alkyl group (in which the heterocyclic moiety having 1 to 2 hetero atoms selected from the group consisting of a nitrogen atom, an oxygen atom and a sulfur atom, and the lower alkyl moiety is substituted with a lower alkoxycarbonyl group), then the corresponding compound (1) in which R4 is a heterocyclic-lower alkyl group (wherein the lower alkyl moiety is substituted with a carboxy group) can be obtained by hydrolyzing the starting compound (1). Said hydrolysis reaction is carried out under the same conditions as those employed in the hydrolysis of a compound (6) in the above-mentioned Reaction scheme-2.

In a compound (1), wherein $R^4$ is a substituted or unsubstituted saturated or unsaturated 5- to 10membered monocyclic or bicyclic heterocyclic-substituted alkyl group (in which the lower alkyl moiety is substituted with a carboxyl group), then the corresponding compound (1) in which R4 is a heterocyclic-substituted lower alkyl group, wherein the lower alkyl moiety is substituted with benzothiazolylaminocarbonyl group can be obtained by reacting said compound (1) with benzothiazolylamine under the same conditions as those employed in the reaction of a compound (2) with a compound (3) as in the above-mentioned Reaction scheme-1.

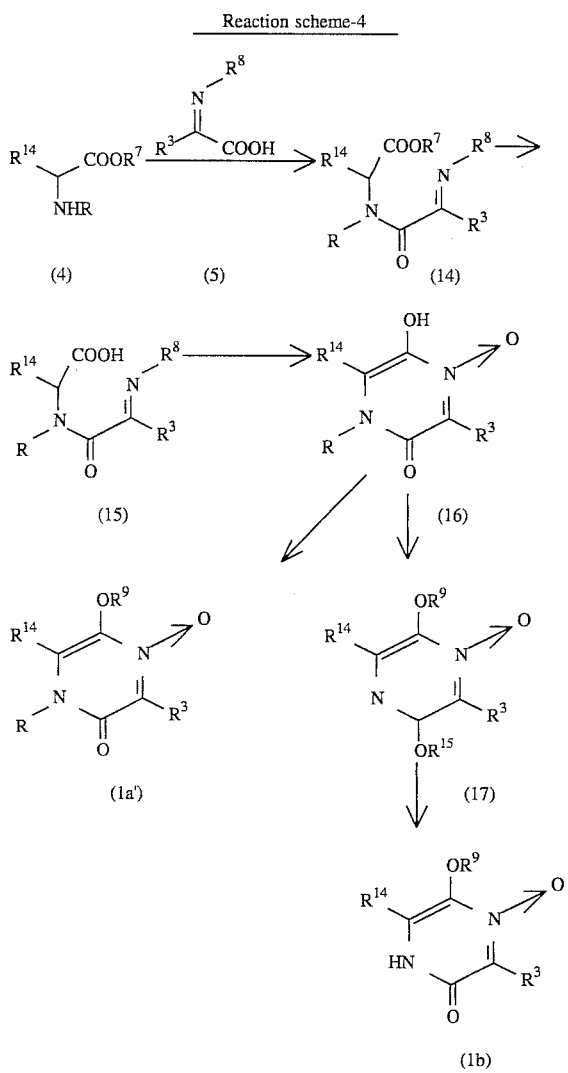

Reaction scheme-4

(wherein R, $R^3$, $R^7$, $R^8$ and $R^9$ are the same as defined above; $R^{14}$ is a phenyl-lower alkyl group which may have, on the phenyl ring, 1 to 3 substituents selected from the group consisting of a lower alkoxy group, a phenyl-lower alkoxy group, a lower alkyl group and a hydroxy group; $R^{15}$ is a silyl group having 1 to 3 substituents selected from the group consisting of a lower alkyl group and a phenyl group).

The reaction of a compound (13) with a compound (5) can be carried out under the same conditions as those employed in the the reaction of a compound (4) with a compound (5) in the above-mentioned Reaction scheme-2.

The reaction of introducing a compound (14) to a compound (15) can be carried out under the same conditions those employed in the reaction of introducing a compound (6) to a compound (7) in the above-mentioned Reaction scheme-2.

The reaction of introducing a compound (15) to a compound (16) can be carried out under the same those employed in the reaction of introducing a compound (7) to a compound (8) in the above-mentioned Reaction scheme-2.

The reaction of introducing a compound (16) to a compound (1a') can be carried out under the same conditions as those employed in the reaction of introducing a compound (8) to a compound (9) in the above-mentioned Reaction scheme-2.

When R in the compound (16) is a hydrogen atom, the reaction of introducing a compound (16) to a compound (17) can be carried out by reacting a compound (16) with a silyl compound, for example an alkylsilyl halide such as tert-butyldimethylsilyl chloride or the like, an alkylsilyl sulfonate such as tert-butyldimethylsilyltrifluoromethyl sulfonate or the like, in a suitable solvent in the presence of a basic compound. As to the basic compound used in the reaction, an organic basic compound such as imidazole, triethylamine, dimethylaminopyridine, 2,6-lutidine, diisopropylethylamine, DBU, DBN and the like exemplified. As to the solvent, a halogenated hydrocarbon such as dichloromethane, chloroform and the like, dimethylformamide, dimethyl sulfoxide and the like can be exemplified. The reaction is carried out. generally at about 0° to 100° C., preferably at about 0° to 70° C., and is completed in 1 to 10 hours. Amount of the silylating agent may be, generally at least in an equimolar quantity, preferably in 1 to 3 times the molar quantity per molar quantity of the starting material.

Next, the thus obtained compound is reacted with an alkylating agent in the absence or presence of a catalyst, in a suitable solvent. As to the solvent used in this reaction, there can be exemplified a lower alcohol such as methanol, ethanol, propyl alcohol of the like; an ether such as dioxane, tetrahydrofuran, diethyl ether, ethylene glycol monomethyl ether or the like; a halogenated hydrocarbon such as dichloromethane, chloroform, carbon tetrachloride or the like; or a mixture of these solvents. As to the catalyst to be used in the reaction, there are exemplified Lewis acids such as boron tribromide, boron trifluoride-diethyl ether and the like. In the case of using diazomethane as the alkylating agent, generally it may be used in a large excess amount, preferably 10 to 20 times of the molar quantity per one molar quantity of the starting material. While, in the case of using other alkylating agent, it may be used in at least an equimolar quantity, preferably an equimolar quantity to 3 times of the molar quantity per one molar quantity of the starting material. As to the alkylating agent, diazomethane, diazoethane, trimethylsilyldiazomethane, a halogenated alkane such as methyl iodide or the like, a lower alkylsulfonic acid ester such as $FSO_3CH_3$, $CF_3SO_3CH_3$, $(CH_3)_2SO_4$ or the like, a lower alkyloxonium halide chelate such as $FSO_3CH_3$, $CF_3SO_3CH_3$, $(CH_3)_2SO_4$ or the like, a lower alkoxyoxonium halide chelate such as $(CH_3)_3O\oplus BF_4\ominus$, $(C_2H_5)_3O\ominus BF_4\ominus$ or the like, a lower alkoxyoxonium halide chelate such as $(C_2H_5)_3\oplus BF_4\ominus$ or the like can be exemplified. The reaction can be carried out, generally at about −30° to 100° C. preferably at about −20° to 70° C., and the reaction is generally completed in 0.5 to 20 hours.

The reaction of introducing a compound (17) to a compound (1b) can be carried out by desilylating reaction. Said desilylating reaction can be carried out in a solvent for example an ether such as tetrahydrofuran, diethyl ether, dioxane or the like, in the presence of a desilylating agent for example, a tetraalkylammonium halide such as tetrabutylammonium fluoride or the like; a fluoride such as hydrofluoric acid, potassium fluoride, cesium fluoride, pyridinium hydrofluoric acid salt or the like; a mineral acid such as hydrochloric acid, hydrobromic acid or the like; an organic acid such as acetic acid; an inorganic base such as potassium carbonate, sodium hydroxide, potassium hydroxide or the like, and generally under a temperature condition of at about −20° to 50° C., preferably at about −20° to 50° C., preferably at about −20° C. to room temperature, and requires for about 10 minutes to 5 hours. The desilylating agent may be used, generally in a large excess amount to the starting material.

Reaction scheme-5

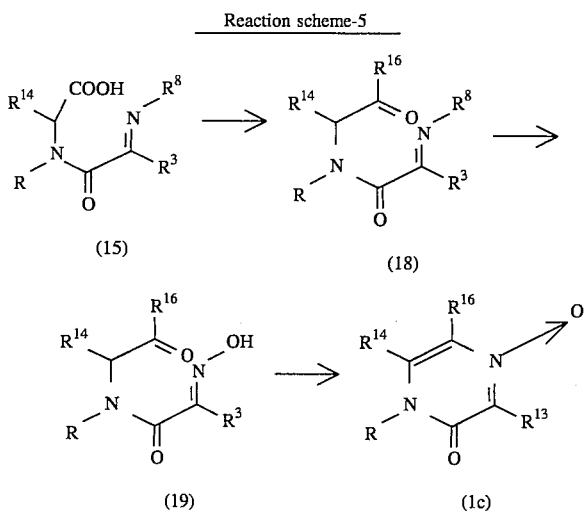

(wherein R, $R^3$, $R^{14}$ and $R^8$ are the same as defined above; $R^{16}$ is a lower alkyl group).

The reaction of introducing a compound (15) to a compound (18) can be carried out in the presence of an acid anhydride and a basic compound, in the absence or presence of a solvent. As to the acid anhydride, a lower alkanoic acid anhydride such as acetic anhydride can be exemplified. As to the basic compound and the solvent, the same type as those employed in the reaction of an acid halide of a carboxylic acid (2) with an amine (3) can be used. As the basic compound, a mixture of the above-mentioned basic compounds can also be used. Amount of the acid anhydride is generally 1 to 15 times the molar quantity, preferably 1 to 10 times of the molar quantity may be used to per mole of a compound (15). Generally, the reaction can be carried out at about 0° to 150° C., preferably at room temperature to 100° C., and is completed in about 1 to 20 hours.

The reaction of introducing a compound (18) to a compound (19) can be carried out under the same reaction conditions as those employed in the reaction of introducing a compound (7) to a compound (7a) in the above-mentioned Reaction scheme-2.

The reaction of introducing a compound (19) to a compound (1c) can be carried out under the same reaction conditions as those employed in the reaction of introducing a compound (11) to a compound (12) in the above-mentioned Reaction scheme-3.

In a compound (1), when $R^4$ and $R^5$ form a piperazine ring by combining the nitrogen atom to which $R^4$ and $R^5$ are directly bonded thereto, together with or without bonding other nitrogen atom, oxygen atom or sulfur atom, then the corresponding compound (1) in which $R^4$ and $R^5$ form a piperazine ring, and the 4-position in the piperazine ring is substituted with a group of $R^{12}$ or $R^{13}$ can be introduced by reacting the unsubstituted piperazine ring in the compound (1) with a compound of the formula $R^{12}X$ (wherein $R^{12}$ as a lower alkoxycarbonyl group; a pyridyl group; a phenyl group which may have 1 to 3 substituents selected from the group consisting of a lower alkoxy group, a lower alkyl group and a lower alkanoyl group, on the phenyl ring; or a phenyl-lower alkyl group which may have 1 to 3 substituents, on the phenyl ring, selected from the group consisting of a lower alkoxy group and a halogen atoms; and X is a halogen atom), or a compound of the formula $R^{13}$-OH (wherein $R^{13}$ is a pyrazinylcarbonyl group which may have, on the pyrazine ring, 1 to 4 substituents selected from the group consisting of an oxo group and a lower alkyl group; a benzoyl group which may have, on the phenyl ring, 1 to 3 substituents selected from the group consisting of a lower alkoxy group and a hydroxy group; a benzoyl group having, on the phenyl ring, a lower alkylenedioxy group as the substituent; a phenyl-lower alkenylcarbonyl group which may have, on the phenyl ring, 1 to 3 substituents selected from the group consisting of a hydroxy group and a lower alkoxy group.).

Among the pyrazine derivatives represented by the formula (1) of the present invention, those having the basic groups can easily be converted into the acid-addition salts by reacting with a pharmaceutically acceptable acid. As to the acid, there can be exemplified an inorganic acid such as hydrochloric acid, sulfuric acid, phosphoric acid, hydrobromic acid or the like; an organic acid such as oxalic acid, acetic acid, succinic acid, malonic acid, methanesulfonic acid, maleic acid, fumaric acid, malic acid, tartaric acid, citric acid, benzoic acid or the like.

Further, among the pyrazine derivatives represented by the formula (1) of the present invention, those having the acidic groups can easily be converted into the salts by reacting with a pharmaceutically acceptable basic compound. As to the basic compound, there can be exemplified such as sodium hydroxide, potassium hydroxide, calcium hydroxide, sodium carbonate, potassium bicarbonate or the like.

The desired products obtained in each one of the reaction steps can easily be isolated and purified by conventional separation means, such as a solvent extraction method, a dilution method, a recrystallization method, a column chromatography method, a preparative thin-layer chromatography method or the like.

The pyrazine derivatives represented by the formula (1) of the present invention include optical isomers and stereo isomers.

The pyrazine derivatives and salts thereof represented by the formula (1) can generally be used in the form of pharmaceutical composition. Such pharmaceutical composition can be prepared by using diluents or excipients such as fillers, diluents, binders, wetting agents, disintegrating agents, surface active agents and lubricants. The pharmaceutical composition can be selected in any desired unit form, including tablets, pills, powders, liquors, suspensions, emulsions, granules, capsules, suppositories, injections (solutions and suspensions) and the like.

For the purpose of shaping in the form of tablets, carriers which are known in this field can be used, for example, excipients such as lactose, sucrose, sodium chloride, glucose, urea, starch, calcium carbonate, kaoline, crystalline cellulose, silicic acid and the like; binding agents such as water, ethanol, propanol, simple syrup, a solution of glucose, a solution of starch, a solution of gelatin, carboxymethyl cellulose, shelac, methylcellulose, potassium phosphate or polyvinylpyrrolidone or the like; disintegrating agents such as dried starch, sodium alginate, agar-agar powder, laminalia powder, sodium bicarbonate, calcium carbonate, esters of polyoxyethylene sorbitan fatty acids, sodium laurylsulfate, monoglyceride of stearic acid, starch, lactose or the like; disintegration inhibitors such as white sugar, stearin, coconut butter, hydrogenated oils or the like; absorption accelerators such as a quaternary ammonium base, sodium laurylsulfate or the like; wetting agents such as glycerin, starch or the like; adsorbing agents such as starch, lactose, kaolin, bentonite, colloidal silicic acid or the like; lubricating agent such as purified talc, stearic acid salts, boric acid powder, polyethylene glycol or the like.

In case of preparing tablets, the tablets can be further coated with an usual coating material to make them as sugar coated tablets, gelatin film coated tablets, tablets coated with enteric coatings, tablets coated with films or double-layered tablets and multi-layered tablets.

For the purpose of shaping in the form of pills, carriers which are known and used widely in this field can be used, for example, excipients such as glucose, lactose, starch, coconut butter, hydrogenated vegetable oils, kaoline or talc or the like; binders such as gum arabic powder, tragacanth gum powder, gelatin, ethanol or the like; disintegrating agents such as laminaria, agar-agar or the like.

For the purpose of shaping in the form of suppositories, carriers which are known and used widely in this field can be used, for example, polyethylene glycols, coconut butter, higher alcohols, esters of higher alcohols, gelatin, semi-synthesized glycerides or the like are included.

For the purpose of shaping in the form of injection preparations, solutions and suspensions are sterilized and are preferably isotonic to the blood. In making the injection preparations, any carriers which are commonly used in this fields can also be used, for example, water, ethyl alcohol, propylene glycol, ethoxylated isostearyl alcohol, polyoxylated isostearyl alcohol, polyoxyethylene sorbitan fatty acid esters or the like are included. In these cases, adequate amount of sodium chloride, glucose, or glycerin can be added to contain in the desired pharmaceutical preparations, for the purpose of having them isotonic solution. Furthermore, usual dissolving agents, buffer solutions, analgesic agents can be added, as well as coloring agents, preservatives, perfumes, seasoning agents, sweetening agents and other medicaments can be added into the desired pharmaceutical preparations, if necessary.

The amount of pyrazine derivative represented by the formula (1) to be contained in the pharmaceutical compositions is not specifically restricted and it can suitably be selected, from a wide range, and generally, 1 to 70% by weight, preferably 1 to 30% by weight of the whole composition may be used.

The above-mentioned pharmaceutical compositions can be administered in various forms depending on the purpose without any restriction, thus the pharmaceutical composition is administered in a suitable method according to the forms of the preparation, the age of the patient, the distinction of sex of the patient, the conditions of the symptoms and other factors. For example, tablets, pills, liquid preparations, suspensions, emulsions granules and capsules are administered orally; and injection preparations are administered intravenously singly or are mixed with injection transfusions such as glucose solutions and amino acid solutions, if necessary the injection preparations are administered singly intramuscularly, intracutanneously, subcutaneously or intraperitoneally; suppoditories are administered into rectum.

The administration dosage of a pharmaceutical composition of the present invention is suitably selected according to the usage, the age of the patient, the distinction of sex of the patient, the condition of the symptoms and other factors, and generally 0.5 to 30 mg per kg of the body weight per day of the pyrazine derivatives of the formula (1) as the active ingredient may be administered, and about 10 to 1,000 mg of the active ingredient may be contained in the administration unit form.

The present invention will be illustrated more specifically by way of the following examples, in which preparation of the compounds to be used as the starting materials will be shown in Reference Examples, and preparation of the desired products will be shown in Examples, Further, Examples of pharmaceutical preparations and Pharmacological test results are also disclosed later.

Reference Example 1

Preparation of Diethyl N-(2-hydroxyimino-4-methylpentanoyl)amino malonate

In to a suspension of 17.5 g of diethyl aminomalonate in 150 ml of dichloromethane, 30 ml of water and 7.0 g of sodium bicarbonate were added, then 20 minutes after, dichloromethane layer was obtained by separation, and was dried with magnesium sulfate. The solvent was removed by distillation under reduced pressure to obtain diethylaminomalonate as a colorless oily product. Then into a solution of thus obtained diethylamino malonate, 10.0 g of α-hydroxyiminoisocapronic acid and 8.7 g of N-hydroxysuccinimide in 200 ml of dioxane, there was added 15.7 g of N,N'-dicyclohexylcarbodiimide, the whole mixture was stirred at room temperature for 16 hours. The reaction mixture was filtrated, the filtrate thus obtained was subjected to distillation for removal of the solvent. To the thus obtained residue was added ethyl acetate, then to the ethyl acetate layer were added with 10% hydrochloric acid, water, an aqueous solution saturated with sodium bicarbonate, and an aqueous solution saturated with sodium chloride in this order for washing, then the ethyl acetate layer was dried with magnesium sulfate. The solvent was removed by distillation to obtain 29.19 g of diethyl N-(2-hydroxyimino- 4-methylpentanoyl)aminomalonate.

Colorless oily product $^1$H-NMR (CDCl$_3$) δ:

0.91 (6H, d, J=6.5Hz), 1.30 (6H, t, J=7Hz), 2.04 (1H, m), 2.52 (1H, d, J=7.5Hz), 4.30 (4H, m), 5.21 (1H, d, J=7Hz), 7.76 (1H, brd, J=7Hz), 8.71 (1H, s).

By using the procedures employed in Reference Example 1 and by using a suitable starting materials, there were prepared compounds as follows:

Diethyl N-(2-hydroxyimino-2-phenylacetyl)aminomalonate

Melting point: 93°–95° C.

White powdery product (Recrystallized from diethyl ether-n-hexane)

Diethyl N-(2-hydroxyimino-3-phenylpropionyl)aminomalonate

Colorless oily product $^1$H-NMR (CDCl$_3$) δ:

1.27 (6H, t, J=7Hz), 3.95 (2H, s), 4.25 (2H, q, J=7Hz), 4.27 (2H, q, J=7Hz), 5.20 (1H, d, 7Hz), 7.13–7.44 (5H, m), 7.79 (1H, d, J=7Hz), 8.91 (1H, brs).

Diethyl N-[2-hydroxyimino-3-(indol-3-yl)propionyl] aminomalonate

Yellow oily product $^1$H-NMR (200 Mhz, CDCl$_3$) δ:

1.26 (6H, t, J=7Hz), 4.07 (2H, s), 4.24 (2H, q, J=7Hz), 4.25 (2H, q, J=7Hz), 5.19 (1H, d, J=7Hz), 7.04 (1H, d, J=2.5Hz), 7.09 (1H, dt, J=7.5Hz, 1.5Hz), 7.16 (1H, dt, J=7.5Hz, 1.5Hz), 7.28 (1H, dd, J=7.5Hz, 1.5Hz), 7.75 (1H, d, J=7.5Hz),7.78 (1H, d, J=7Hz), 7.96 (1H, brs), 8.56 (1H, brs).

Reference Example 2

Synthesis of N-(2-hydroxyimino-4-methylpentanoyl)aminomalonic acid monoethyl ester In to a solution of 29.19 g of diethyl N-(2-hydroxyimino-4-methylpentanoyl)aminomalonate in 200 ml of ethanol was added 2.8 g of sodium hydroxide and 200 ml of water, then the mixture was stirred at room temperature for 4 hours. The reaction mixture was neutralized with 10% hydrochloric acid, then concentrated. To the residue thus obtained was added 10% hydrochloric acid to make it acidified, then it was extracted with ethyl acetate, and the ethyl acetate layer was washed with water, an aqueous solution saturated with sodium chloride in this order, then dried with magnesium sulfate. The solvent was removed by distillation to obtain 23.0 of N-(2-hydroxyimino-4-methylpentanoyl)aminomalonic acid monoethyl ester.

Pale yellow solid product
$^1$H-NMR (CDCl$_3$) δ:
0.91 (6H, d, J=6.5Hz), 1.32 (3H, d, J=7.0Hz), 2.56 (1H, m), 2.52 (2H, d, J=8.0Hz), 4.31 (2H, q, J=7.0Hz), 5.26 (1H, d, J=7.5Hz), 7.85 (1H, brd, J=7.5Hz).

By using the procedures employed in Reference Example 2, and by using a suitable starting materials, there were prepared compounds as follows:

N-(2-Hydroxyimino-2-phenylacetyl)aminomalonic acid monoethyl ester
Melting point: 95°–96° C.
Colorless prism (Recrystallization from dichloromethane-n-hexane)

N-(2-Hydroxyimino-3-phenylpropionyl)aminomalonic acid monoethyl ester
Melting point: 132°–133° C.
White powdery product N-[2-Hydroxyimino-3-(indol-3-yl)propionyl] aminomalonic acid monoethyl ester
Melting point: 82°–85° C.
White powdery product
$^1$H-NMR (250 MHz, DMSO-d$_6$) δ:
1.25 (3H, t, J=7Hz), 3.87 (2H, s), 4.13 (2H, q, J=7Hz), 4.92 (1H, d, J=6.5Hz), 6.94 (1H, t, J=7Hz), 7.02 (1H, d, J=2.5Hz), 7.03 (1H, t, J=7Hz), 7.30 (1H, d, J=8Hz), 7.60 (1H, d, J=7.5Hz), 7.89 (1H, d, J=6.5Hz), 10.82 (1H, brs), 12.14 (1H, s).

Reference Example 3

Synthesis of 6-ethoxycarbonyl-5-hydroxy-3-isobutyl-1,2-dihydropyrazine-2-one 4-oxide Into a solution of 23.0 g of N-(2-hydroxy-imino- 4-methylpentanoyl)aminomalonic acid monoethyl ester in 600 ml of dichloromethane was added 15.2 g of 2,2-dipyridylsulfide at 0° C., further 18.1 g of triphenylphosphine was added thereto, then the reaction mixture was stirred at room temperature for 1.5 hours. The reaction mixture was extracted with 2.5% aqueous solution of potassium hydrogen sulfate, an aqueous solution saturated with sodium chloride and an aqueous solution saturated with sodium bicarbonate, then washed with ethyl acetate. Then it is acidified with a concentrated hydrochloric acid, and the crystals precipitated were collected by filtration to obtain 9.28 g of 6-ethoxycarbonyl-5-hydroxy-3-isobutyl-1,2-dihydropyrazin- 2-one 4-oxide.

Yellowish solid product
Melting point: 153°–155° C.

By using the procedures employed in Reference Example 3 and by using suitable starting materials there were prepared the following compounds:

8-Ethoxycarbonyl-5-hydroxy-3-phenyl-1,2-dihydropyrazin- 2-one 4-oxide
Yellow powdery product
$^1$H-NMR (250 MHz, DMSO-d$_6$) δ:
1.32 (3H, t, J=7Hz), 4.34 (2H, q, J=7Hz), 7.45–7.55 (3H, m), 7.60–7.70 (2H, m).

6-Ethoxycarbonyl-5-hydroxy-3-benzyl-1,2-dihydropyrazine- 2-one 4-oxide
Melting point: 147°–149° C.

Yellow needle-like crystals
6-Ethoxycarbonyl-5-hydroxy-3-(indol-3-yl)methyl- 1,2-dihydropyrazin-2-one 4-oxide
Melting point: 154°–155° C.
Yellow powdery product
$^1$H-NMR (250 MHz, DMSO-d$_6$) δ:
1.25 (3H, t, J=7Hz), 4.22 (2H, s), 4.26 (2H, q, J=7Hz), 6.95 (1H, t, J=7Hz), 7.04 (1H, t, J=7Hz), 7.21 (1H, d, J=2.5Hz), 7.31 (1H, d, J=8Hz), 7.70 (1H, d, J=7.5Hz), 10.92 (1H, s).

Reference Example 4

Synthesis of 6-ethoxycarbonyl-3-isobutyl-5-methoxy-1,2-dihydropyrazin-2-one 4-oxide To a suspension of 5.45 g of 6-ethoxycarbonyl- 5-hydroxy-3-isobutyl-1,2-dihydropyrazin-2-one 4-oxide in chloroform was added dropwise gradually about equivalent quantity of diethyl ether solution of diazomethane at −15° C. 30 Minutes after the addition, 0.5 ml of acetic acid was added to the reaction mixture, and this mixture was allowed to stand for 30 minutes. Then the whole mixture was washed with water, and the solvent was removed by distillation, to the thus obtained residue was added 30 ml of chloroform and dissolved by heating, then 200 ml of diisopropyl ether was added gradually thereto so as to form crystals. The precipitated crystals were collected by filtration, and said operation were repeated twice to obtain 3.10 g of 6-ethoxycarbonyl-3-isobutyl-5-methoxy-1,2-dihydropyrazin- 2-one 4-oxide.

Melting point: 153°–155° C.
Pale yellow solid material

By using the procedures employed in Reference Example 4, and by using suitable starting materials, there were prepared compounds as follows:

6-Ethoxycarbonyl-3-phenyl-5-methoxy-1,2-dihydropyrazin- 2-one 4-oxide
Melting point: 147°–149° C.
Yellow powdery product (Recrystallized from dichloromethane-n-hexane)

6-Ethoxycarbonyl-3-benzyl-5-methoxy-1,2-dihydropyrazin- 2-one 4-oxide
Melting point: 150°–152° C.
Colorless needle-like crystals (Recrystallized form diethyl ether)

6-Ethoxycarbonyl-3-(indol-3-yl)methyl-5-methoxy- 1,2-dihydropyrazin-2-one 4-oxide
Melting point: 186°–188° C.
Yellow needle-like crystals (Recrystallized from dichloromethane)

6-Ethoxycarbonyl-3-phenyl-5-methoxy-1-methyl- 1,2-dihydropyrazin-2-one 4-oxide
Melting point: 106°–110° C.
Yellow needle-like crystals (Recrystallized from diethyl ether-n-hexane)

Reference Example 5

Synthesis of 3-isobutyl-5-methoxy-1,2-dihydropyrazin-2-one-6-carboxylic acid 4-oxide 932 Milligrams of 6-ethoxycarbonyl-3-isobutyl- 5-methoxy-1,2-dihydropyrazin-2-one 4-oxide in 21 ml of methanol and 10 ml of an aqueous solution of 1N-sodium hydroxide were mixed and stirred at room temperature for hours. The reaction mixture was acidified by adding hydrochloric acid, and the precipitated crystals were collected by filtration, and the crystals were dissolved in chloroform-methanol, next the solvent was removed by distillation to obtain 830 mg of 3-isobutyl- 5-methoxy-1,2-dihydropyrazin-2-one-6-carboxylic acid 4oxide.

White solid product
$^1$H-NMR (CDCl$_3$) δ:

0.98 (6H, d, J=6.5Hz), 2.28 (1H, m), 2.84 (2H, d, J=7Hz), 4.04 (3H, s).

By using the procedures as those employed in Reference Example 5, and by using a suitable starting material, there was prepared compound as follows:

1-Methyl-3-phenyl-5-methoxy-1,2-dihydropyrazin-2-one-6-carboxylic acid 4-oxide

Pale yellow powdery product $^1$H-NMR (250 MHz, CDCl$_3$) δ:

3.53 (3H, s), 4.01 (3H, s), 4.82 (1H. br), 7.45–7.55 (3H, m), 7.70–7.80 (2H, m).

Reference Example 6

To a solution of 8.62 g of α-hydroxyiminoisocapronic acid and 7.18 g of N-hydroxysuccinimide in 100 ml of dried dioxane was added 12.26 g of DCC, and the mixture was stirred at room temperature for 2 hours. The DCC was removed by filtration, and the thus obtained filtrate was added to 90 ml of dried dioxane suspension containing 8.89 g of methyl 2-aminopropionylacetate hydrochloride and 7.3 ml of triethylamine, then the mixture was stirred at room temperature for 18 hours. The reaction mixture was diluted with ethyl acetate, and was washed with 1N-hydrochloric acid, an aqueous solution saturated with sodium chloride, an aqueous solution saturated with sodium bicarbonate, then an aqueous solution saturated with sodium chloride in this order, and dried with magnesium sulfate. The solvent was removed by distillation, and the thus obtained residue was purified by means of a silica gel column chromatography (eluent: n-hexane:ethyl acetate=4:1), then recrystallized from n-hexane to obtain 10.39 g of 2-[N-(2-hydroxyimino-4-methyl)pentanoyl] amino-3-oxopentanic acid methyl ester.

Colorless plate-like crystals

Melting point: 79°–81° C.

Reference Example 7

59.2 Grams of 2-[N-(2-hydroxyimino-4-methyl)pentanoyl] amino-3-oxopentanoic acid methyl ester was dissolved in 300 ml of trifluoroacetic acid, and stirred at 50°–55° C. for 2.5 hours. The solvent was removed by distillation under reduced pressure at 30° C., and the the resulting residue was dissolved in diethyl ether. The diethyl ether solution was washed with an aqueous solution saturated with sodium chloride three times, then washed with an aqueous solution saturated with sodium bicarbonate and was dried with magnesium sulfate. The solvent was removed by distillation and the resulting residue was purified by means of a silica gel column chromatography (eluent: n-hexane:ethyl acetate=4:1), then recrystallized from diethyl ether-n-hexane to obtaining 32.6 g of 5-ethyl-3-isobutyl-6-methoxycarbonyl- 1,2-dihydropyrazin-2-one 4-oxide. In the purification by means of a silica gel chromatography as above, 32.6 g of 2-[N-(2-hydroxyimino-4-methyl)pentanoyl] amino-3-oxopentanoic acid methyl ester was also recovered.

Colorless needle-like crystals

Melting point: 143°–146° C.

Reference Example 8

To a solution of 7.99 g of 5-ethyl-3-isobutyl- 6-methoxycarbonyl-1,2-dihydropyrazin-2-one 4-oxide in ml of methanol was added 63 ml of 2N-sodium hydroxide aqueous solution, and the mixture was stirred at room temperature for 2 hours. The solvent was removed by distillation under reduced pressure, and the resulting residue was dissolved in water, then under ice-cooling condition with stirring, the solution was acidified by adding 11 ml of concentrated hydrochloric acid. The crystals thus precipitated were collected by filtration, and were washed with water, then recrystallized from dichloromethanemethanol to obtain 6.24 g of 5-ethyl-3-isobutyl-1,2-dihydropyrazin-2-one-6-carboxylic acid 4-oxide.

Pale yellow plate-like crystals

Melting point: 209°–212° C.

Reference Example 9

By using the same procedures as those employed in Reference Example 5 and by using suitable starting materials, there were prepared compounds as follows:

3-Benzyl-5-methoxy-1,2-dihydropyrazin-2-one-6-carboxylic acid 4-oxide

White powdery product $^1$H-NMR (DMSO-d$_6$) δ ppm:

3.86 (3H, s), 4.08 (2H, s), 7.05–7.45 (5H, m)

3-(Indol-3-yl)methyl-5-methoxy-1,2-dihydropyrazin-2-one-6-carboxylic acid 4-oxide Yellow powdery product $^1$H-NMR (DMSO-d$_6$) δ ppm:

3.86 (3H, s), 4.15 (2H, s), 8.94 (1H, t, J=7.5Hz ), 7.03 ( 1H, t, J=7.5Hz ), 7.22 (1H, d, J=2Hz), 7.30 (1H, d, J=7.5Hz), 7.71 (1H, d, J=7.5Hz), 10.87 (1H, s)

Reference Example 10

To a solution of 34.47 g of 3,4,5-trimethoxyphenylalanine methyl ester, 18.87 g of α-hydroxyiminoisocaproic acid, 14.96 g of N-hydroxysuccinimide in 1 liter of dioxane, was added 26.82 g of N,N'-dicyclohexylcarbodiimide, and the mixture was stirred at room temperature for 18 hours. The reaction mixture was filtrated, and the filtrate was subjected to distillation to remove the solvent. The resulting residue was purified by means of a silica gel column chromatography (eluent: ethyl acetate:n-hexane=1:2) to obtain 42.70 g of N-(2-hydroxyimino-4-methylpentanoyl)-( 3,4,5-trimethoxy-y)phenylalanine methyl ester.

White powdery product $^1$H-NMR (CDCl$_3$) δ:

0.90 (6H, d, J=6.5Hz), 1.90–2.11 (1H, m), 2.52 (2H, d, J=7.5Hz), 3.08 (2H, ddd, J=15Hz, 9Hz, 6Hz), 3.74 (3H, s), 3.81 (6H, s), 3.82 (3H, s), 4.91 (1H, dt, J=8.5Hz, 6Hz), 6.32 (2H, s), 7.17 (1H, d, J=8.5Hz), 7.83 (1H, brs).

Reference Example 11

By using the same procedures as those employed in Reference Example 10, and by using suitable starting materials, there were prepared compounds as follows:

N-(2-Hydroxyimino-4-methylpentanoyl)-L-phenylalanine methyl ester

Colorless needled-like crystals

Melting point: 71°–73° C.

N-(2-Hydroxyimino-4-methylpentanoyl)-O-benzyl-L-tyrosine methyl ester

Colorless needle-like crystals

Melting point: 108°–110° C.

N-(2-Hydroxyimino-4-methylpentanoyl)-(3,5-di-tert-butyl)tyrosine ethyl ester

White powdery product $^1$H-NMR (CDCl$_3$) δ:

0.90 (6H, dd, J=6.5Hz, 1Hz), 1.21 (3H, t, J=7Hz), 1.28 (18H, s), 1.80–2.15 (1H, m), 2.52 (2H, d, J=7.5Hz), 3.04 (2H, ddd, 16.5Hz, 13.5Hz, 6Hz), 4.000–4.23 (2H, m), 4.82 (1H, dt, J=8Hz, 6Hz), 5.10 (1H, s), 6.89 (2H, s), 7.15 (1H, brd, J=8.5Hz), 7.56 (1H, brs).

Reference Example 12

To an ethanol solution (500 ml) of 31.98 g of N-(2-hydroxyimino-4-methylpentanoyl)-(3,4,5-trimethoxy)phenylalanine methyl ester was added 180 ml of 1N-sodium hydroxide aqueous solution, and the mixture was stirred at room temperature for 13 hours. After the removal of the solvent by distillation, the residue was acidified by adding with a hydrochloric acid, then was extracted with ethyl acetate. The ethyl acetate layer was washed with an aqueous solution saturated with sodium chloride and was dried with magnesium sulfate. By removal of the solvent by distillation, 30.93 g of N-(2-hydroxyimino-4-methylpentanoyl)-(3,4,5-trimethoxy)phenylalanine was obtained.

White powdery product
$^1$H-NMR (CDCl$_3$) δ:
0.85 (3H, d, J=6.5Hz), 0.86 (3H, d, J=6.5Hz), 1.88–2.07 (1H, m), 2.49 (2H, ddd, J=19.5Hz, 12.5Hz, 5Hz), 3.12 (2H, ddd, J=38Hz, 14Hz, 6Hz), 3.77 (6H, s), 3.80 (3H, s), 4.92 (1H, dt, J=8.5Hz, 6Hz), 6.38 (2H, s), 7.28 (1H, d, J=8.5Hz).

Reference Example 13

By the same procedures as those employed in Reference Example 12, and by using suitable starting materials, there were prepared compound as follows:

N-(2-Hydroxyimino-4-methylpentanoyl)-L-phenylalanine
White powdery product
Melting point: 120°–122° C.

N-(2-Hydroxyimino-4-methylpentanoyl)-O-benzyl-L-tyrosine
Colorless needle-like crystals
Melting point: 147°–148° C.

N-(2-Hydroxyimino-4-methylpentanoyl)-(3,5-di-tert-butyl)tyrosine
Brown powdery product
$^1$H-NMR (CDCl$_3$) δ:
0.60–1.04 (6H, m), 1.36 (18H, s), 1.80–2.04 (1H, m), 2.47–2.53 (2H, m), 2.91–3.11 (1H, m), 3.17–3.38 (1H, m), 4.78–4.95 (1H, m), 5.11 (1H, s), 6.94 (2H, s), 7.28 (1H, s), 7.0–7.7 (1H, brs).

Reference Example 14

To a solution of 7.50 g of N-(2-hydroxyimino- 4-methylpentanoyl)-(3,4,5-trimethoxy)phenylalanine methyl ester in dried dimethylformamide (150 ml) was added 0.9 g of sodium hydride (60%), and the mixture was stirred at room temperature for 1 hour. Then 2.75 ml of benzyl bromide was added to the reaction mixture and further stirred at room temperature for 2 hours. The reaction mixture was transferred to an aqueous solution saturated with ammonium chloride under an ice-cooling condition, then was extracted with ethyl acetate. The organic layer was washed with an aqueous solution saturated with sodium chloride in three times, and was dried with magnesium sulfate, and the solvent was removed by distillation, the resulting residue was purified by means of a silica gel column chromatography (eluent: ethyl acetate:n-hexane=1:3) to obtain 8.35 g of N-(2-benzyloxyimino-4-methylpentanoyl)-(3,4,5-trimethoxy)phenylalanine methyl ester.

White powdery product
$^1$H-NMR (CDCl$_3$) δ:
0.86 (6H, dd, J=6.5Hz, 1Hz), 1.87–2.12 (1H, m), 2.49 (2H, d, J=7Hz), 3.08 (2H, ddd, J=17Hz, 10.5Hz, 6Hz), 3.74 (3H, s), 3.78 (6H, s), 3.82 (3H, s), 4.87 (1H, dt, J=8Hz, 6Hz), 5.15 (2H, s), 6.32 (2H, s), 7.16 (1H, d, J=8Hz), 7.27–7.53 (5H, m).

Reference Example 15

To an ethanol solution (100 ml) containing 6.43 g of N-(2-benzyloxyimino-4-methylpentanoyl)-(3,4,5-trimethoxy)-phenylalanine methyl ester was added 15 ml of 1N-sodium hydroxide aqueous solution, and was stirred at room temperature for 12 hours. After removal of the solvent by distillation, the residue was acidified by adding hydrochloric acid, then was extracted with ethyl acetate. The ethyl acetate layer was washed with an aqueous solution saturated with sodium chloride, then dried with magnesium sulfate. The solvent was removed by distillation to obtain 5.69 g of N-(2-benzyloxyimino 4-methylpetanoyl)-(3,4,5-trimethoxy)phenylalanine.

White powdery product
$^1$H-NMR (CDCl$_3$) δ:
0.86 (6H, d, J=6.5Hz), 1.88–2.06 (1H, m), 2.48 (2H, d, J=7.5Hz), 3.14 (2H, ddd, J=30Hz, 14Hz, 6.5Hz), 3.78 (6H, s), 3.82 (3H, s), 4.86 (1H, dt, J=8Hz, 6.5Hz), 5.14 (2H, s), 6.39 (2H, s), 7.13 (1H, d, J=8Hz), 7.26–7.52 (5H, m).

Reference Example 16

To a triethylamine solution (120 ml) containing 5.67 g of N-(2-benzyloxyimino-4-methylpentanoyl)-( 3,4,5-trimethoxy)phenylalanine, there was added 6 ml of propionic anhydride and 0.15 g of 4-dimethylaminopyridine, and reflexed for 2 hours. The reaction mixture was dried under reduced pressure, and to the residue was added ethyl acetate and water, then the organic layer was obtained by separation, and was dried with magnesium sulfate. After the removal of the solvent by distillation, the resulting residue was dissolved in 180 ml of methanol, then 6.6 g of potassium carbonate was added thereto and stirred at room temperature for 18 hours. After removal of the solvent by distillation, thus obtained residue was purified by means of a silica gel column chromatography (eluent: ethyl acetate:n-hexane= 1:2) to obtain 1.74 g of 2-[N-( 2-benzyloxyimino-4-methylpentanoyl)amino]-1-(3,4,5-trimethoxy)phenylpentan-3-one.

Pale yellow powdery product
$^1$H-NMR (CDCl$_3$) δ:
0.85 (3H, d, J=6.5Hz), 0.86 (3H, d, J=6.5Hz), 1.00 (3H, t, J=7Hz), 1.89–2.05 (1H, m), 2.37 (2H, q, J=7Hz), 2.48 (2H, d, J=7Hz), 3.00 (2H, d, J=7Hz), 3.79 (6H, s), 3.82 (3H, s), 4.82 (1H, dt, J=8Hz, 7Hz), 5.16 (2H, s), 6.34 (2H, s), 7.29–7.52 (6H, m).

Example 1

1.00 Gram of 3-isobutyl-5-methoxy-1,2-dihydro-pyrazin-2-one-6-carboxylic acid 4-oxide, 0.57 g of m-methoxybenzylamine and 0.52 g of N-hydroxysuccinimide were dissolved in 40 ml of dried dioxane, then 0,94 g of N,N'-dicyclohexylcarbodiimide (DCC) was added to the reaction mixture and stirred at room temperature for 16 hours. After the reaction was completed, the insoluble matters were removed by filtration, and the resulting filtrate was concentrated under reduced pressure to dryness. The residue thus obtained was purified by means of a silica gel column chromatography (eluent: methanol: chloroform=1:50), and was recrystallized from methanoldiisopropyl ether to obtain 1.5 g of 3-isobutyl-5-methoxy- 6-N-(3-methoxybenzyl) carbamoyl-1,2-dihydro-pyrazin- 2-one 4-oxide.

White powdery product,
Melting point: 156°–159° C.

Example 2–44

By using the procedures similar to those employed in Example 1, and by using suitable starting materials, there were prepared compounds of Examples 2– 44 as follows:

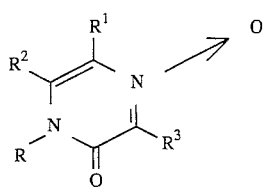

Example 2

Structure:

$R^1$: —OCH$_3$, $R^3$: —CH$_2$CH(CH$_3$)$_2$

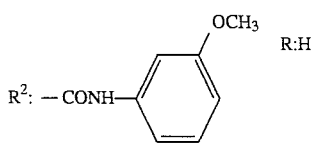

Melting point: 142°–147° C.
Crystal form: Pale yellowish powdery product
Recrystallization solvent: Methanol-diisopropyl ether Example 3

Structure:

$R^1$: —OCH$_3$, $R^3$: —CH$_2$CH(CH$_3$)$_2$

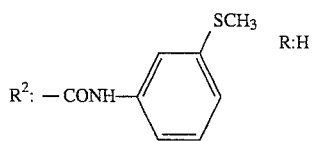

Melting point: 149°–150° C.
Crystal form: Yellowish prisms
Recrystallization solvent: Ethyl acetate-n-hexane Example 4

Structure:

$R^1$: —OCH$_3$, $R^3$: —CH$_2$CH(CH$_3$)$_2$

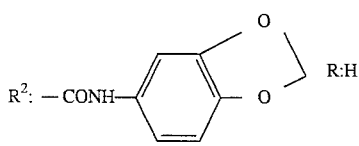

Melting point: 194° C. (decomposed)
Crystal form: Yellowish powdery product
Recrystallization solvent: Dimethylformamide-water Example 5

Structure:

$R^1$: —OCH$_3$, $R^3$: —CH$_2$CH(CH$_3$)$_2$

-continued

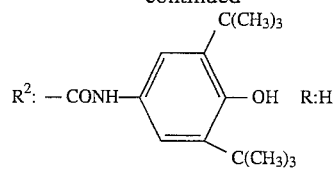

Melting point: 185° C. (decomposed)
Crystal form: Pale yellowish powdery product
Recrystallization solvent: Methanol-diisopropyl ether Example 6

Structure:

$R^1$: —OCH$_3$, $R^3$: —CH$_2$CH(CH$_3$)$_2$

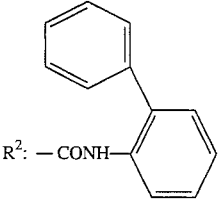

Melting point: 144°–146° C.
Crystal form: Yellowish needle-like crystals
Recrystallization solvent: Dichloromethane-diethyl ether Example 7

Structure:

$R^1$: —OCH$_3$, $R^3$: —CH$_2$CH(CH$_3$)$_2$

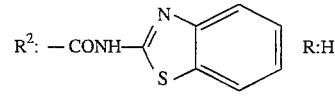

Melting point: 180° C. (decomposed)
Crystal form: Yellowish powdery product
Recrystallization solvent: Methanol Example 8

Structure:

$R^1$: —OCH$_3$, $R^3$: —CH$_2$CH(CH$_3$)$_2$

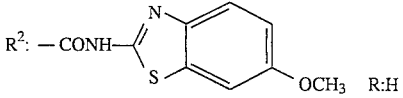

Melting point: 189° C. (decomposed)
Crystal form: Yellowish needle-like crystals
Recrystallization solvent: Methanol Example 9

Structure:

$R^1$: —OCH$_3$, $R^3$: —CH$_2$CH(CH$_3$)$_2$

-continued

R²: —CONH— 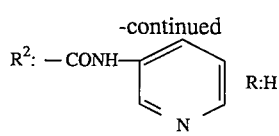 R:H

Melting point: 158° C. (decomposed)
Crystal form: Yellowish powdery product
Recrystallization solvent: Methanol-dichloromethane Example 10

Structure:

R¹: —OCH₃, R³: —CH₂CH(CH₃)₂

R²: —CONH— 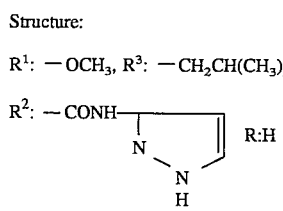 R:H

Melting point: 201°–202° C.
Crystal form: Pale yellowish needle-like crystals
Recrystallization solvent: Methanol Example 11

Structure:

R¹: —OCH₃, R³: —CH₂CH(CH₃)₂

R²: —CONH— 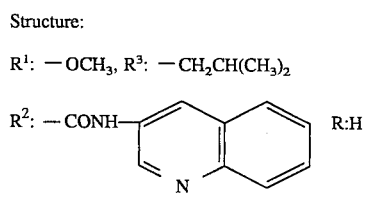 R:H

Melting point: 176° C. (decomposed)
Crystal form: Orange powdery product
Recrystallization solvent: Methanol Example 12

Structure:

R¹: —OCH₃, R³: —CH₂CH(CH₃)₂

R²: —CONH— 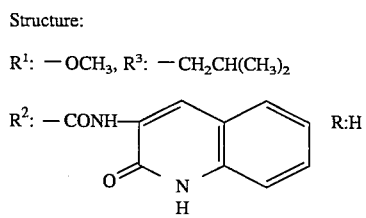 R:H

Melting point: 224° C. (decomposed)
Crystal form: Pale yellowish needle-like crystals
Recrystallization solvent: Dimethyl sulfoxide Example 13

Structure:

R¹: —OCH₃, R³: —CH₂CH(CH₃)₂

R²: —CONH— 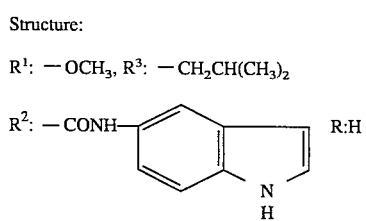 R:H

Melting point: 191° C. (decomposed)
Crystal form: Pale yellowish needle-like crystals
Recrystallization solvent: Methanol Example 14

Structure:

R¹: —OCH₃, R³: —CH₂CH(CH₃)₂

R²: —CONH— 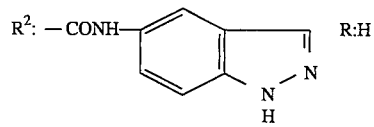 R:H

Melting point: 214°–215° C.
Crystal form: Yellowish needle-like crystals
Recrystallization solvent: Methanol Example 15

Structure:

R¹: —OCH₃, R³: —CH₂CH(CH₃)₂

R²: —CONHCH₂CH— 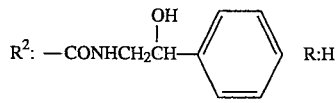 R:H

Melting point: 161°–163° C.
Crystal form: Colorless needle-like crystals
Recrystallization solvent: Ethanol Example 16

Structure:

R¹: —OCH₃, R³: —CH₂CH(CH₃)₂

R²: —CONHCH₂— 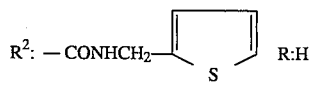 R:H

Melting point: 167°–167.5° C. (decomposed)
Crystal form: Colorless needle-like crystals
Recrystallization solvent: Methanol Example 17

Structure:

R¹: —OCH₃, R³: —CH₂CH(CH₃)₂

R²: —CONHCH₂— 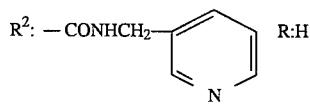 R:H

Melting point: —NMR[1]
Crystal form: Yellowish foams
Recrystallization solvent:

Example 18

Structure:

R¹: —OCH₃, R³: —CH₂CH(CH₃)₂

R²: —CONHCH₂— 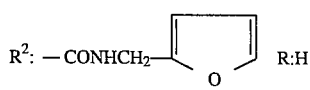 R:H

Melting point: 177°–179° C.
Crystal form: Pale yellowish needle-like crystals

Recrystallization solvent: Methanol-diisopropyl ether
Example 19

Structure:

R$^1$: —OCH$_3$, R$^3$: —CH$_2$CH(CH$_3$)$_2$

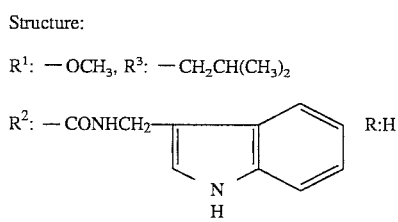

R$^2$: —CONHCH$_2$—     R:H

Melting point: 122°–129° C.
Crystal form: Pale yellowish powdery product
Recrystallization solvent: Methanol-diisopropyl ether
Example 20

Structure:

R$^1$: —OCH$_3$, R$^3$: —CH$_2$CH(CH$_3$)$_2$

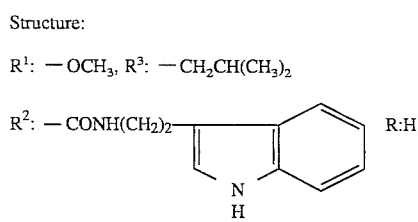

R$^2$: —CONH(CH$_2$)$_2$—     R:H

Melting point: 204° C. (decomposed)
Crystal form: Pale yellowish prisms
Recrystallization solvent: Methanol
Example 21

Structure:

R$^1$: —OCH$_3$, R$^3$: —CH$_2$CH(CH$_3$)$_2$

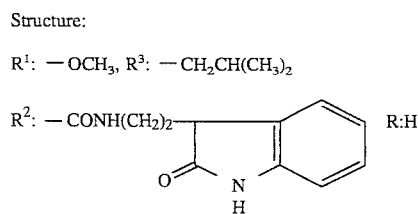

R$^2$: —CONH(CH$_2$)$_2$—     R:H

Melting point: 189° C. (decomposed)
Crystal form: Pale yellowish powdery product
Recrystallization solvent: Methanol
Example 22

Structure:

R$^1$: —OCH$_3$, R$^3$: —CH$_2$CH(CH$_3$)$_2$

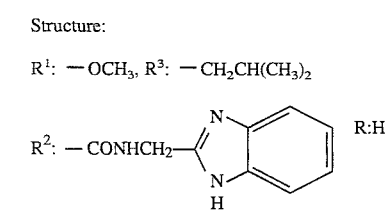

R$^2$: —CONHCH$_2$—     R:H

Melting point: 195° C. (decomposed)
Crystal form: Yellowish needle-like crystals
Recrystallization solvent: Methanol
Example 23

Structure:

-continued

R$^1$: —OCH$_3$, R$^3$: —CH$_2$CH(CH$_3$)$_2$

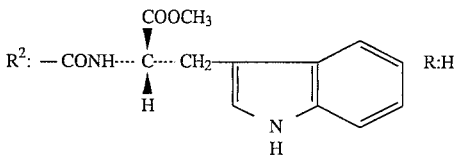

Melting point: 90°–94° C.
Crystal form: Yellowish plate-like crystals
Recrystallization solvent: Dichloromethane-diethyl ether
Example 24

Structure:

R$^1$: —OCH$_3$, R$^3$: —CH$_2$CH(CH$_3$)$_2$

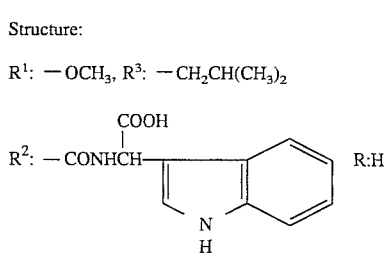

Melting point: 191°–192° C.
Crystal form: Brown powdery product
Recrystallization solvent: 50% Ethanol-water
Example 25

Structure:

R$^1$: —OCH$_3$, R$^3$: —CH$_2$CH(CH$_3$)$_2$

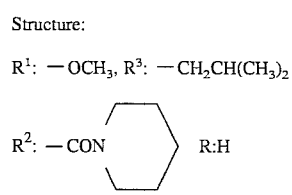

R$^2$: —CON     R:H

Melting point: 129.5°–131° C.
Crystal form: White powdery product
Recrystallization solvent: Diisopropyl ether
Example 26

Structure:

R$^1$: —OCH$_3$, R$^3$: —CH$_2$CH(CH$_3$)$_2$

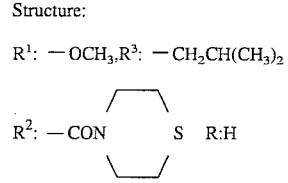

R$^2$: —CON    S    R:H

Melting point: 178.5°–179° C.
Crystal form: White powdery product
Recrystallization solvent: Diethyl ether
Example 27

Structure:

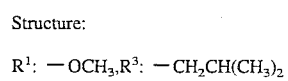

R$^1$: —OCH$_3$, R$^3$: —CH$_2$CH(CH$_3$)$_2$

-continued

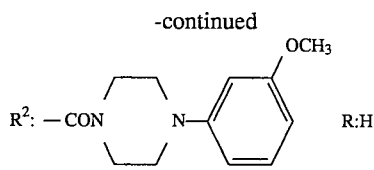 R:H

Melting point: 172° C. (decomposed)
Crystal form: Pale yellowish powdery product
Recrystallization solvent: Diethyl ether
Example 28

Structure:

$R^1$: —OCH$_3$, $R^3$: —CH$_2$CH(CH$_3$)$_2$

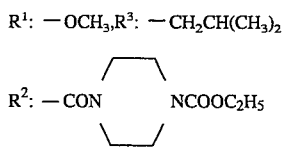 R:H

Melting point: 151°–152° C.
Crystal form: Colorless prisms
Recrystallization solvent: Diethyl ether
Example 29

Structure:

$R^1$: —OCH$_3$, $R^3$: —CH$_2$CH(CH$_3$)$_2$ $R^2$: —CONH$_2$ R:H

Melting point: 206°–210° C.
Crystal form: Pale yellowish needle-like crystals
Recrystallization solvent: Methanol-diethyl ether
Example 30

Structure:

$R^1$: —OCH$_3$, $R^3$: —CH$_2$CH(CH$_3$)$_2$ $R^{20}$: —CONHCH$_3$ R:H

Melting point: 162° C. (decomposed)
Crystal form: Yellowish leaves
Recrystallization solvent: Methanol-diethyl ether
Example 31

Structure:

$R^1$: —OCH$_3$, $R^3$: —CH$_2$CH(CH$_3$)$_2$

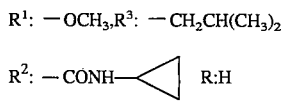 R:H

Melting point: 161.5°–163° C.
Crystal form: Pale yellowish needle-like crystals
Recrystallization solvent: Dichloromethane-diethyl ether
Example 32

Structure:

$R^1$: —OCH$_3$, $R^3$: —CH$_2$CH(CH$_3$)$_2$

-continued

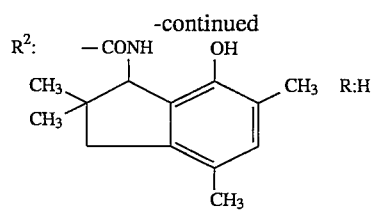 R:H

Melting point: 176°–182° C.
Crystal form: White powdery product
Recrystallization solvent: Diethyl ether
Example 33

Structure:

$R^1$: —C$_2$H$_5$, $R^3$: —CH$_2$CH(CH$_3$)$_2$

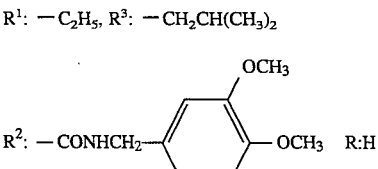 R:H

Melting point: 191°–192° C.
Crystal form: Colorless needle-like crystals
Recrystallization solvent: Ethanol
Example 34

Structure:

$R^1$: —C$_2$H$_5$, $R^3$: —CH$_2$CH(CH$_3$)$_2$

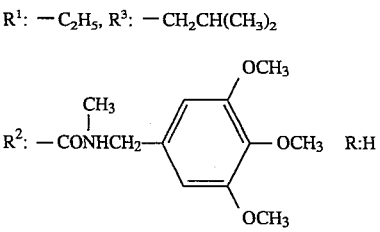 R:H

Melting point: 166°–168° C.
Crystal form: Colorless prisms
Recrystallization solvent: Ethanol
Example 35

Structure:

$R^1$: —C$_2$H$_5$, $R^3$: —CH$_2$CH(CH$_3$)$_2$

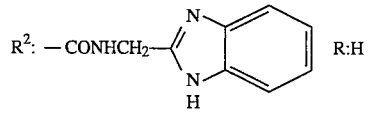 R:H

Melting point: 232°–234° C.
Crystal form: Colorless needle-like crystals
Recrystallization solvent: Ethanol
Example 36

Structure:

$R^1$: —C$_2$H$_5$, $R^3$: —CH$_2$CH(CH$_3$)$_2$

-continued

R²: 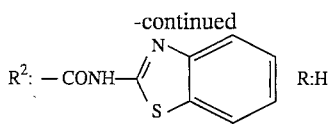 R:H

Melting point: 230°–232° C.
Crystal form: Pale yellowish needle-like crystals
Recrystallization solvent: Ethyl acetate
Example 37

Structure:

R¹: —C₂H₅, R³: —CH₂CH(CH₃)₂

R²: 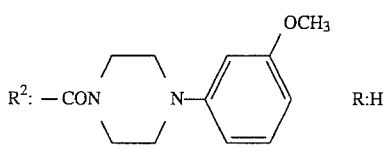 R:H

Melting point: 157°–158° C.
Crystal form: Colorless needle-like crystals
Recrystallization solvent: Diethyl ether
Example 38

Structure:

R¹: —C₂H₅, R³: —CH₂CH(CH₃)₂

R²: 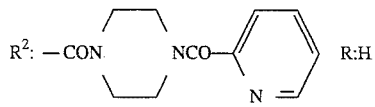 R:H

Melting point: 193°–195° C.
Crystal form: Pale yellowish prisms
Recrystallization solvent: Ethanol
Example 39

Structure:

R¹: —C₂H₅, R³: —CH₂CH(CH₃)₂

R²: 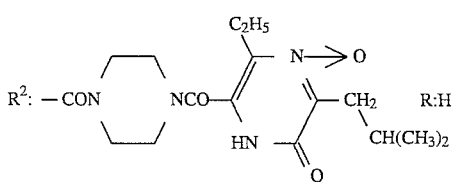 R:H

Melting point: 275°–278° C.
Crystal form: Colorless prisms
Recrystallization solvent: Dichloromethane-methanol
Example 40

Structure:

R¹: —C₂H₅, R³: —CH₂CH(CH₃)₂

R²: 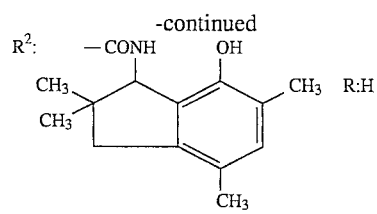 R:H

Melting point: 194°–195° C.
Crystal form: Colorless needle-like crystals
Recrystallization solvent: Diethyl ether
Example 41

Structure:

R¹: —OCH₃, R₃: 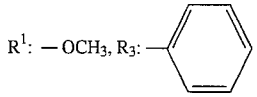

R²: 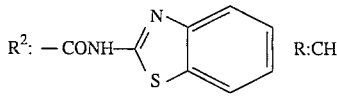 R:CH₃

Melting point: 171°–174° C.
Crystal form: Yellowish powdery product
Recrystallization solvent: Dichloromethane-diethyl ether
Example 42

Structure:

R¹: —OCH₃, R³: —CH₂CH(CH₃)₂

R²: 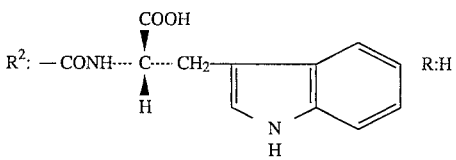 R:H

Melting point: 175° C. (decomposed)
Crystal form: White powdery product
Recrystallization solvent:
Example 43

Structure:

R¹: —OCH₃, R³: —CH₂CH(CH₃)₂

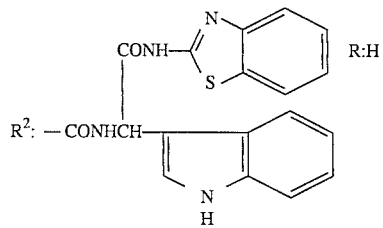 R:H

Melting point: 203° C. (decomposed)
Crystal form: Brown powdery product
Recrystallization solvent: Diethyl ether Example 44

Structure:

$R^1$: —OCH$_3$, $R^3$: —CH$_2$CH(CH$_3$)$_2$ $R^2$: —CONHCH$_2$— 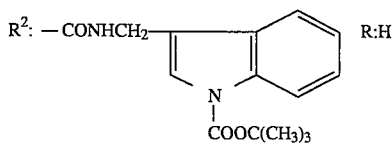 R:H Crystal form: Pale yellowish oily product NMR$^{(2)}$
NMR $^{(1)}$ $^1$H-NMR (250MHz, DMSO-d$_6$) δ:
0.99 (6H, d, J=7Hz), 2.23 (1H, m), 2.76 (2H, d, J=7.5Hz), 3.96 (3H, s), 4.58 (2H, d, J=6Hz), 7.48 (1H, dd, J=8Hz, 5Hz), 7.84 (1H, d, J=8Hz), 8.58 (1H, d, J=5Hz), 8.67 (1H, s), 9.16 (1H, brt, J=6Hz).
NMR $^{(2)}$ $^1$H-NMR (250MHz, CDCl$_3$) δ:
0.97 (6H, J=7Hz), 1.68 (9H, s), 2.26 (1H, m), 2.84 (2H, d, J=7.5Hz), 3.93 (3H, s), 4.78 (2H, d, J=5.5Hz), 7.26 (1H, t, J-7Hz), 7.37 (1H, t, J=7Hz), 7.54 (1H, d, J=7Hz), 7.63 (1H, s), 7.82 (1H, brt, J=5.5Hz), 8.14 (1H, d, J=7Hz).

Examples 45–86

By using procedures similar to those employed in Example 1, and by using suitable starting materials, there were prepared compounds of Examples 45–86 as shown in Table 1 as follows:

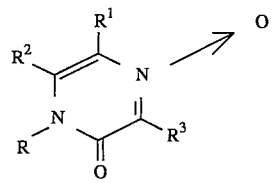

TABLE 1

| Example No. | R | $R^1$ | $R^2$ | $R^3$ | Crystal form (Recrystallization solvent) | Melting point (°C.) |
|---|---|---|---|---|---|---|
| 45 | H | —OCH$_3$ | —CONHCH$_2$—(2-OCH$_3$-C$_6$H$_4$) | —CH$_2$CH(CH$_3$)$_2$ | Colorless-needles(Ethanol) | 190–192 |
| 46 | H | —OCH$_3$ | —CONHCH$_2$—(4-OCH$_3$-C$_6$H$_4$) | —CH$_2$CH(CH$_3$)$_2$ | Colorless-needles(Ethanol) | 170–171 |
| 47 | H | —OCH$_3$ | —CONHCH$_2$—(2,3-(OCH$_3$)$_2$-C$_6$H$_3$) | —CH$_2$CH(CH$_3$)$_2$ | Colorless-needles(Ethanol) | 179–181 |
| 48 | H | —OCH$_3$ | —CONHCH$_2$—(3,4-(OCH$_3$)$_2$-C$_6$H$_3$) | —CH$_2$CH(CH$_3$)$_2$ | Colorless-needles(Ethanol) | 159–160 |
| 49 | H | —OCH$_3$ | —CONHCH$_2$—(2,4-(OCH$_3$)$_2$-C$_6$H$_3$) | —CH$_2$CH(CH$_3$)$_2$ | Colorless-needles(Ethanol) | 173–175 |
| 50 | H | —OCH$_3$ | —CONHCH$_2$—(2,5-(OCH$_3$)$_2$-C$_6$H$_3$) | —CH$_2$CH(CH$_3$)$_2$ | Colorless-needles(Ethanol) | 190–193 |

TABLE 1-continued

| Example No. | R | R¹ | R² | R³ | Crystal form (Recrystallization solvent) | Melting point (°C.) |
|---|---|---|---|---|---|---|
| 51 | H | —OCH₃ | —CONHCH₂—(2,6-dimethoxyphenyl) | —CH₂CH(CH₃)₂ | Colorless plates (Ethanol) | 180–181 |
| 52 | H | —OCH₃ | —CONHCH₂—(3-methoxy-4-benzyloxyphenyl) | —CH₂CH(CH₃)₂ | Yellow plates (Ethanol) | 175–176 |
| 53 | H | —OCH₃ | —CONHCH₂—(3-methoxy-4-hydroxyphenyl) | —CH₂CH(CH₃)₂ | Colorless needles (Ethanol-diethyl ether) | 174–175 |
| 54 | H | —OCH₃ | —CONHCH₂—(3,4,5-trimethoxyphenyl) | —CH₂CH(CH₃)₂ | Colorless needles (Ethanol) | 188–190 |
| 55 | H | —OCH₃ | —CONHCH₂—(3,5-dimethoxy-4-benzyloxyphenyl) | —CH₂CH(CH₃)₂ | Colorless needles (Ethanol) | 177–178 |
| 56 | H | —OCH₃ | —CONHCH₂—(3,5-dimethoxy-4-hydroxyphenyl) | —CH₂CH(CH₃)₂ | Pale yellow needles (Ethanol-diethyl ether) | 175–177 |
| 57 | H | —OCH₃ | —CONHCH₂—(3,5-di-tert-butyl-4-hydroxyphenyl) | —CH₂CH(CH₃)₂ | Colorless needles (Diethyl ether-n-hexane) | 111–113 |
| 58 | H | —OCH₃ | —CONHCH₂—(2-fluorophenyl) | —CH₂CH(CH₃)₂ | Pale yellow needles (Ethanol) | 157–159 |
| 59 | H | —OCH₃ | —CONHCH₂—(3,5-diethoxyphenyl) | —CH₂CH(CH₃)₂ | Pale yellow flakes (Ethanol) | 171–173 |

TABLE 1-continued

| Example No. | R | R¹ | R² | R³ | Crystal form (Recrystallization solvent) | Melting point (°C.) |
|---|---|---|---|---|---|---|
| 60 | H | —OCH₃ | —CONHCH₂—(2,4-dichlorophenyl) | —CH₂CH(CH₃)₂ | Pale yellow-needles(Ethanol) | 186–188 |
| 61 | H | —OCH₃ | —CONH(CH₂)₂—(3-methoxyphenyl) | —CH₂CH(CH₃)₂ | Pale yellow-needles(Ethanol) | 124–125 |
| 62 | H | —OCH₃ | —CONH(CH₂)₂O—(4-methoxyphenyl) | —CH₂CH(CH₃)₂ | Pale yellow-needles(Ethanol) | 165–166 |
| 63 | H | —OCH₃ | —CON(CH₃)(CH₂—(3-methoxyphenyl)) | —CH₂CH(CH₃)₂ | Pale yellow powder | 52–54 |
| 64 | H | —OCH₃ | —CON(piperazinyl)-(2-methoxyphenyl) | —CH₂CH(CH₃)₂ | Colorless-flakes(Ethanol) | 196–198 |
| 65 | H | —OCH₃ | —CON(piperazinyl)-(4-methoxyphenyl) | —CH₂CH(CH₃)₂ | Colorless-needles(Ethanol) | 186–188 |
| 66 | H | —OCH₃ | —CON(piperazinyl)-(3,4-dimethoxyphenyl) | —CH₂CH(CH₃)₂ | Colorless-needles(Ethanol) | 174–175 |
| 67 | H | —OCH₃ | —CON(piperazinyl)-C(=O)-(2-methoxyphenyl) | —CH₂CH(CH₃)₂ | Colorless-flakes(Ethanol-diethyl ether) | 193–194 |
| 68 | H | —OCH₃ | —CON(piperazinyl)-C(=O)-(3-methoxyphenyl) | —CH₂CH(CH₃)₂ | Colorless-flakes(Ethanol-diethyl ether) | 150–152 |
| 69 | H | —OCH₃ | —CON(piperazinyl)-C(=O)-(2,4-dimethoxyphenyl) | —CH₂CH(CH₃)₂ | Colorless-flakes(Ethanol-diethyl ether) | 190–191 |

TABLE 1-continued

| Example No. | R | R¹ | R² | R³ | Crystal form (Recrystallization solvent) | Melting point (°C.) |
|---|---|---|---|---|---|---|
| 70 | H | —OCH₃ | —CON〈piperazine〉N—C(=O)—(3,4-methylenedioxyphenyl) | —CH₂CH(CH₃)₂ | Pale yellow-flakes(Dichloromethane-n-hexane) | 118–120 |
| 71 | H | —OCH₃ | —CON〈piperazine〉N—CH₂—(2-methoxyphenyl) | —CH₂CH(CH₃)₂ | Pale yellow-prisms(Ethanol-diethyl ether) | 143–143.5 |
| 72 | H | —OCH₃ | —CON〈piperazine〉N—CH₂—(3-methoxyphenyl) | —CH₂CH(CH₃)₂ | Pale yellow-needles(Ethanol-diethyl ether) | 165–167 |
| 73 | H | —OCH₃ | —CON〈piperazine〉N—CH₂—(2,4-dimethoxyphenyl) | —CH₂CH(CH₃)₂ | Colorless-flakes(Ethanol-diethyl ether) | 163–163.5 |
| 74 | H | —OCH₃ | —CON〈piperazine〉N—(2-ethoxyphenyl) | —CH₂CH(CH₃)₂ | Colorless-needles(Ethanol) | 161–162 |
| 75 | H | —OCH₃ | —CON〈piperazine〉N—(4-acetylphenyl) | —CH₂CH(CH₃)₂ | Pale yellow-flakes(Ethanol) | 186–186.5 |
| 76 | H | —OCH₃ | —CON〈piperazine〉N—(2-methoxy-3-methylphenyl) | —CH₂CH(CH₃)₂ | Pale yellow-prisms(Ethanol) | 187–189 |
| 77 | H | —OCH₃ | —CON〈piperazine〉N—CH₂—(2,4-dichlorophenyl) | —CH₂CH(CH₃)₂ | Colorlessflakes-(Diethylether) | 144–146 |
| 78 | H | —OCH₃ | —CONH—C(=N)(benzothiazole) | —CH₂—(phenyl) | Yellowneedles-(Methanol) | 184–186 |
| 79 | H | —OCH₃ | —CONH—C(=N)(benzothiazole) | —(CH₂)₂CH=CH₂ | Yellowpowder-(Methanol) | 250(decomposed) |
| 80 | H | —OCH₃ | —CONHCH₂—(2-methoxyphenyl) | —(CH₂)₂CH=CH₂ | Yellowpowder-(Ethylacetate) | 154–155 |

TABLE 1-continued

| Example No. | R | R¹ | R² | R³ | Crystal form (Recrystallization solvent) | Melting point (°C.) |
|---|---|---|---|---|---|---|
| 81 | H | —OCH₃ | —CONHCH₂—(3-OCH₃-phenyl) | —(CH₂)₂CH=CH₂ | Pale yellow-needles(Ethylacetate) | 169–169.5 |
| 82 | H | —OCH₃ | —CON(piperazinyl)—(3-OCH₃-phenyl) | —(CH₂)₂CH=CH₂ | Colorlessneedled(Ethylacetate) | 153–154 |
| 83 | H | —OCH₃ | —CON(piperazinyl)—(3,4-diOCH₃-phenyl) | —(CH₂)₂CH=CH₂ | Pale yellowpowder(Diisopropylether) | 155–155.5 |
| 84 | H | —OCH₃ | —CON(piperazinyl)N—C(O)—(3,5-diOCH₃-4-OH-phenyl) | —CH₂CH(CH₃)₂ | Whitepowder(Ethanol) | 202–204 |
| 85 | H | —OCH₃ | —CON(piperazinyl)N—C(O)—CH=CH—(4-OH-3-OCH₃-phenyl) | —CH₂CH(CH₃)₂ | Whitepowder(Ethanol) | 221–222 |
| 86 | H | —OCH₃ | —CON(piperidinyl) | —CH₂-(indol-3-yl) | Yellowpowder | 127–129 |

Example 87

To a suspension (90 ml) of dried dichloromethane, containing 3.00 g of 5-hydroxy-3-isobutyl-6-(3,4,5-trimethoxybenzyl)-1,2-dihydropyrazin-2-one 4-oxide, there were added 1.16 g of tert-butyldimethylsilyl chloride and 1.05 g of imidazole, and the mixture was stirred at room temperature for 18 hours. The reaction mixture was washed with an aqueous solution saturated with sodium chloride and was dried with magnesium sulfate. After filtration of the reaction mixture, to the filtrate was added a diethyl ether solution of diazo-methane, then this mixture was allowed to stand at room temperature for 1.5 hours. The solvent was removed by distillation under reduced pressure, the resulting residue was dissolved in 50 ml of tetrahydrofuran and 5 ml of methanol, then 5 ml of tetrahydrofuran solution of 1M-n-Bu₄N⊕F⊖ was added thereto and was stirred at room temperature for 10 minutes. To this reaction mixture was added ethyl acetate and water, then the organic layer was obtained by separation and dried with magnesium sulfate. The solvent was removed by distillation, and the residue thus obtained was purified by means of a silica gel column chromatography (eluent: dichloromethane), and the pale yellow oily substance was crystallized from diethyl ether to obtain 0.74 g of 3-isobutyl-5-methoxy-6-(3,4,5-trimethoxybenzyl)-1,2dihydro pyrazin-2-one 4-oxide. Pale yellow needles Melting point: 134°–135° C.

Examples 88–92

By using procedures similar to those employed in Example 87, and by using suitable starting materials, there were prepared compounds of Example 88–92 as shown in the Table 2 as follows:

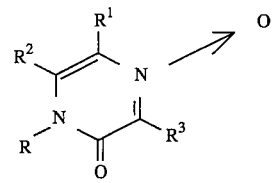

TABLE 2

| Example No. | R | R¹ | R² | R³ | Crystal form (Recrystallization solvent) | Melting point (°C.) |
|---|---|---|---|---|---|---|
| 88 | H | —OCH₃ | —CH₂—C₆H₅ | —CH₂CH(CH₃)₂ | Colorless needles(Methanol) | 189.5–190.5 |
| 89 | H | —OCH₃ | —CH₂—C₆H₄—OCH₂—C₆H₅ | —CH₂CH(CH₃)₂ | Colorless needles(Chloroform-methanol) | 205–207 |
| 90 | H | —OCH₃ | —CH₂—C₆H₄—OH | —CH₂CH(CH₃)₂ | Colorless needles(Ethyl acetate-methanol) | 215–217 |
| 91 | H | —OC₂H₅ | —CH₂—C₆H₂(OCH₃)₃ | —CH₂CH(CH₃)₂ | Pale yellow needles | 144–144.5 |
| 92 | H | —OCH₃ | —CH₂—C₆H₂(C(CH₃)₃)₂—OH | —CH₂CH(CH₃)₂ | Colorless needles(Diethyl ether) | 182–183 |

Example 93

To a dioxane solution (200 ml) containing 18.71 of N-(2-hydroxyimino-4-methylpentanoyl)-(3,4,5-trimethoxy)phenylalanine and 6.04 g of N-hydroxysuccinimide, was added 18.83 g of N,N'-dicyclohexylcarbodiimide, and the mixture was stirred at room temperature for 12 hours. After the reaction mixture was filtered, to the filtrate thus obtained was added 4.31 g of sodium acetate, then this mixture was stirred at room temperature for 5 hours. Then the reaction mixture was transferred to 600 ml of ice-water containing 5 ml of acetic acid, the precipitated semi-solid was collected and was dissolved in dichloromethane, the insoluble matters were removed by filtration, the organic layer was washed with in aqueous solution saturated with sodium chloride, then dried with magnesium sulfate. The solvent was removed by distillation to obtain yellow semi-solid, then 30 ml of diethyl ether was added and the mixture was allowed to stand for 2 days in a refrigerator to crystallize. The solid matter was collected by filtration and washed with diethyl ether to obtain 6.11 g of 5-hydroxy-3-isobutyl- 6-(3,4,5-trimethoxybenzyl)-1,2-dihydropyrazin- 2-one 4-oxide as yellow powder.

¹H-NMR (DMSO-d₆) δ:

0.90 (6H, d, J=6.5Hz), 2.04–2.23 (1H, m), 2.64 (2H, d, J=6.5Hz), 3.62 (3H, s), 3.74 (6H, s), 3.88 (2H, s), 6.61 (2H, s).

Example 94

By using procedures similar to those employed in Example 93, and by using suitable starting materials, there were prepared compounds as follows:

6-Benzyl-5-hydroxy-3-isobutyl-1,2-dihydro-pyrazin-2-one 4-oxide

Yellow powder

Melting point: 174°–176° C.

6-(4-Benzyloxybenzyl)-5-hydroxy-3-isobutyl,2-dihydropyrazin- 2-one 4-oxide

Yellow powder

¹H-NMR (DMSO-d₆) δ:

0.89 (6H, d, J=7Hz), 2.03–2.23 (1H, m), 2.63 (2H, d, J=7.5Hz), 3.86 (2H, s), 5.07 (2H, s) , 6.10 (1H, brs), 6.93 (2H, d, J=8.5Hz), 7.20 (2H, d, J=8.5Hz), 7.28–7.55 (5H, m).

6-(3,5-Di-tert-butyl-4-hydroxy)benzyl-5-hydroxy-3-isobutyl-1,2-dihydropyrazin-2-one 4-oxide Yellow powder ¹H-NMR (CDCl₃) δ:

0.99 (6H, d, J=6.5Hz), 1.41 (18H, s), 2.20– 2.37 (1H, m), 2.85 (2H, d, J=7.5Hz), 3.92 (2H, s), 5.20 (1H, brs), 7.24 (2H, s).

Example 95

1.87 Grams of 2-[N-(2-benzyloxyimino-4-methylpentanoyl] -amino-1-(3,4,5-trimethoxy)phenylpentan-3-one was dissolved in 35 ml of ethanol and 35 ml of dimethylformamide, then 0.7 ml of trifluoroacetic acid and 0.2 g of 10% palladium-carbon were added thereto, then the reaction mixture was subjected to catalytic reduction at room temperature for 5 hours, further at 50° C. for 5 hours. The catalyst was removed by filtration, and the filtrate was concentrated under reduced pressure. The residue thus obtained was dissolved in 50 ml of methanol, next 0.36 g of p-toluenesulfonic acid monohydrate was added and refluxed for 90 hours. After removal of the solvent by distillation, the residue was purified by means of a silica gel column chromatography (eluent: ethyl acetate:n-hexane=1:2), then recrystallized from ethanol to obtain 0.72 g of 5-ethyl-3- isobutyl- 6-(3,4,5-trimethoxybenzyl)-1,2-dihydropyrazin-2one 4-oxide.

Colorless prisms

Melting point: 126.5°–127° C.

Example of Pharmaceutical Preparation

A pharmaceutical composition containing a pyrazine derivative of the formula (1) of the present invention as the active ingredient was prepared with the following formulation.

| | |
|---|---|
| 3-Isobutyl-5-methoxy-6-N-(3-methoxy-benzyl) carbamoyl-1,2-dihydropyrazin-2-one 4-oxide | 150.0 g |
| Citric acid | 1.0 g |
| Lactose | 33.5 g |
| Dicalcium phosphate | 70.0 g |
| Pluronic F-68 (Trademark for a polyoxyalkylene glycol, manufactured by BASF-Wyandott Corp., N.J., U.S.A.) | 30.0 g |
| Sodium laurylsulfate | 15.0 g |
| polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dried sodium laurylsulfate | 3.0 g |
| Dried magnesium stearate | 3.0 g |
| Ethanol | q. s. |

The pyrazine derivative of the present invention, citric acid, lactose, dicalcium phosphate, Pluronic F-68 and sodium laurylsulfate were admixed together thoughly to obtain a mixture. The mixture thus obtained was sieved through a screen No. 60, then such sieved powder of the mixture was subjected to wet-granulation with an ethanolic solution containing polyvinylpyrrolidone, Carbowax 1500 and Carbowax 6000. The powder of mixture was shaped into a paste-like pump by adding an adequate amount of ethanol, if necessary. Corn starch was added to this lump and well kneaded to form the lump into granules having uniform particle size. The granules thus obtained were sieved through a screen of No 10, then the sieved granules were placed on a tray and dried in an oven at 100° C. for 12 to 14 hours. The dried granules were sieved through a screen of No. 16, and were added thereto dried sodium laurylsulfate and dried magnesium stearate, then the whole mixture was mixed well and was compressed into the desired form by using a tablet machine to obtain tablets to be used for the core portions of coated tablets.

The cored portions were treated with a varnish, and further the treated surface thereof were coated with talc for preventing the surface from the adsorption of moisture. The treated surface of core portions were further coated with a primary coating layer, and further coated with a varnish to make a sufficient number of layer for preventing coated tablets for oral administration. In order to make the coated core portions of tablets into complete spherical form and to make the treated surface smoothly, the coated tablets were further coated with primary coating layers and smoothing the coating layers. The coated tablets were color coated until the desired color of the surface was obtained. After the coated tablets were dried, the surface thereof were polished to make them uniform gloss.

Pharmacological Tests

By using the following test compounds, the pharmacological tests were conducted.

| Test compound No. | |
|---|---|
| (1) | 3-Isobutyl-5-methoxy-6-[N-(3-methoxybenzyl)]-carbamoyl-1,2-dihydropyrazin-2-one 4-oxide |
| (2) | 3-Isobutyl-5-methoxy-6-[N-(3-methoxypheny)]-carbamoyl-1,2-dihydropyrazin-2-one 4-oxide |
| (3) | 3-Isobutyl-5-methoxy-6[-N-(3-methylthio-pheny)]-carbamoyl-1,2-dihydropyrazin-2-one 4-oxide |
| (4) | 3-Isobutyl-5-methoxy-6-[N-(3,4-methylenedioxy-phenyl)]carbamoyl-1,2-dihydropyrazin-2-one 4-oxide |
| (5) | 3-Isobutyl-5-methoxy-6-[N-(3,5,-di-tert-butyl-4-hydroxyphenyl)]carbamoyl-1,2-dihydropyrazin-2-one 4-oxide |
| (6) | 3-Isobutyl-5-methoxy-6-[N-(2-biphenyl)]-carbamoyl-1,2-dihydropyrazin-2-one 4-oxide |
| (7) | 3-Isobutyl-5-methoxy-6-[N-(benzothiazol-2-y)]-carbamoyl-1,2-dihydropyrazin-2-one 4-oxide |
| (8) | 3-Isobutyl-5-methoxy-6-[N-(6-methoxybenzo-thiazol-2-yl)]carbamoyl-1,2-dihydropyrazin-2-one 4-oxide |
| (9) | 3-Isobutyl-5-methoxy-6-[N-(carbostyril-3-yl)]-carbamoyl-1,2-dihydropyrazin-2-one 4-oxide |
| (10) | 3-Isobutyl-5-methoxy-6-[N-(indol-5-yl)]-carbamoyl-1,2-dihydropyrazin-2-one 4-oxide |
| (11) | 3-Isobutyl-5-methoxy-6-N-(benzopyrazol-5-yl)carbamoyl-1,2-dihydropyrazin-2-one 4-oxide |
| (12) | 3-Isobutyl-5-methoxy-6-[N-(pyridin-3-yl)-methyl]-carbamoyl-1,2-dihydropyrazin-2-one 4-oxide |
| (13) | 3-Isobutyl-5-methoxy-6-[N-(furan-2-yl)methyl]-carbamoyl-1,2-dihydropyrazin-2-one 4-oxide |
| (14) | 3-Isobutyl-5-methoxy-6-[N-(indol-3-yl)-methyl]-carbamoyl-1,2-dihydropyrazin-2-one 4-oxide |
| (15) | 3-Isobutyl-5-methoxy-6-{N-[2-(indol-3-yl)]-ethyl}-carbamoyl-1,2-dihydropyrazin-2-one 4-oxide |
| (16) | 3-Isobutyl-5-methoxy-6-{N-[2-(2-oxyindol-3-yl)-ethyl]}carbamoyl-1,2-dihydropyrazin-2-one 4-oxide |
| (17) | 3-Isobutyl-5-methoxy-6-[N-(benzimidazol-2-yl)-methyl]carbamoyl-1,2-dihydropyrazin-2-one 4-oxide |
| (18) | 3-Isobutyl-5-methoxy-6-{N-[(S)-1-methoxy-carbonyl-2-(indol-3-yl)ethyl]}carbamoyl-1,2-dihydrpyrazin-2-one 4-oxide |
| (19) | 3-Isobutyl-5-methoxy-6-{N-[1-carboxy-1-(indol-3-yl)methyl]}carbamoyl-1,2-dihydropyrazin-2-one 4-oxide |
| (20) | 3-Isobutyl-5-methoxy-6-{N-(1-[(benzothiazol-2-yl)carbamoy]-1-(indol-3-yl)methyl))}carbamoyl-1,2-dihydropyrazin-2-one 4-oxide |
| (21) | 3-Isobutyl-5-methoxy-6-[(1-piperidinyl)carboxy]-1,2-dihydropyrazin-2-one 4-oxide |
| (22) | 3-Isobutyl-5-methoxy-6-methylcarbamoyl-1,2-dihydropyrazin-2-one 4-oxide |
| (23) | 3-Isobutyl-5-methoxy-6-cyclopropylcarbamoyl-1,2-dihydropyrazin-2-one 4-oxide |
| (24) | 3-Isobutyl-5-methoxy-6-[N-(2,3-dihydro-7-hydroxy-2,2,4,6-tetramethyl-1H-inden-1-yl)]carbamoyl-1,2-dihydropyrazin-2-one 4-oxide |
| (25) | 3-Isobutyl-5-ethyl-6-[N-(benzothiazol-2-yl)]-carbamoyl-1,2-dihydropyrazin-2-one 4-oxide |
| (26) | 3-Isobutyl-5-ethyl-6-[4-(3-methoxyphenyl)-1-piperazinyl]carbonyl-1,2-dihydropyrazin-2-one 4-oxide |
| (27) | 3-Isobutyl-5-ethyl-6-[N-(pyridin-2-yl)-1-piperazinyl]carbonyl-1,2-dihydropyrazin-2-one 4-oxide |
| (28) | 3-Isobutyl-5-methoxy-6-{N-[(S)-1-carboxyl-2-indol-3-yl)ethyl]}carbonyl-1,2-dihydropyrazin-2-one 4-oxide |
| (29) | 3-Isobutyl-5-methoxy-6-[N-(2,6-dimethoxy-benzyl)]-carbamoyl-1,2-dihydropyrazin-2-one 4-oxide |
| (30) | 3-Isobutyl-5-methoxy-6-[N-(3-methoxy-4-hydroxybenzyl)]carbamoyl-1,2-dihydropyrazin-2- |

(31) 3-Isobutyl-5-methoxy-6-[N-(3,4,5-trimethoxy-benzyl)]carbamoyl-1,2-dihydropyrazin-2-one 4-oxide
(32) 3-Isobutyl-5-methoxy-6-[N-(3,5-dimethoxy-4-benzyloxybenzyl)]carbamoyl-1,2-dihydropyrazin-2-one 4-oxide
(33) 3-Isobutyl-5-methoxy-6-[N-(3,5-dimethoxy-4-hydroxybenzyl)]carbamoyl-1,2-dihydropyrazin-2-one 4-oxide
(34) 3-Isobutyl-5-methoxy-6-[N-(3,5-di-tert-butyl-4-hydroxybenzyl)]carbamoyl-1,2-dihydropyrazin-2-one 4-oxide
(35) 3-Isobutyl-5-methoxy-6-[N-(2-fluorobenzyl)]-carbamoyl-1,2-dihydropyrazin-2-one 4-oxide
(36) 3-Isobutyl-5-methoxy-6-[N-(2,4-diethoxy-benzyl)]-carbamoyl-1,2-dihydropyrazin-2-one 4-oxide
(37) 3-Isobutyl-5-methoxy-6-[N-(2,4-dichloro-benzyl)]carbamoyl-1,2-dihydropyrazin-2-one 4-oxide
(38) 3-Isobutyl-5-methoxy-6-{N-[2-(3-methoxy-phenyl)-ethyl]}carbamoyl-1,2-dihydropyrazin-2-one 4-oxide
(39) 3-Isobutyl-5-methoxy-6-{N-[2-(4-methoxyphenoxy)ethyl]}carbamoyl-1,2-dihydropyrazin-2-one 4-oxide
(40) 3-Isobutyl-5-methoxy-6-[N-methyl-N-(3-methoxybenzyl)]carbamoyl-1,2-dihydropyrazin-2-one 4-oxide
(41) 3-Isobutyl-5-methoxy-6-[4-(2-methoxyphenyl)-1-piperazinyl]carbonyl-1,2-dihydropyrazin-2-one 4-oxide
(42) 3-Isobutyl-5-methoxy-6-[4-(4-methoxyphenyl)-1-piperazinyl]carbonyl-1,2-dihydropyrazin-2-one 4-oxide
(43) 3-Isobutyl-5-methoxy-6-[4-(3,4-dimethoxy-phenyl-1-piperazinyl] carbonyl-1,2-dihydro-pyrazin-2-one 4-oxide
(44) 3-Isobutyl-5-methoxy-6-[4-(4-acetylphenyl)-1-piperazinyl]carbonyl-1,2-dihydropyrazin-2-one 4-oxide
(45) 3-Isobutyl-5-methoxy-6-[4-(2,4-dichloro-benzyl)-1-piperazinyl]carbonyl-1,2-dihydro-pyrazin-2-one 4-oxide
(46) 3-Benzyl-5-methoxy-6-[N-(benzothiazol-2-yl)]-carbamoyl-1,2-dihydropyrazin-2-one 4-oxide
(47) 3-(3-Butenyl)-5-methoxy-6-[N-(benzothiazol-2-yl)]carbamoyl-1,2-dihydropyrazin-2-one 4-oxide
(48) 3-(3-Butenyl)-5-methoxy-6-[N-(2-methoxybenzyl)]carbamoyl-1,2-dihydropyrazin-2-one 4-oxide
(49) 3-(3-Butenyl)-5-methoxy-6-[4-(3-methoxy-phenyl)-1-piperazinyl]carbonyl-1,2-dihydro-pyrazin-2-one 4-oxide
(50) 3-(3-Butenyl)-5-methoxy-6-[4-(3,4-dimethoxy-phenyl)-1-piperazinyl]carbonyl-1,2-dihydro-pyrazin-2-one 4-oxide
(51) 3-Isobutyl-5-methoxy-6-[4-(3,5-dimethoxy-4-hydroxybenzoyl)-1-piperaziny]carbonyl-1,2-dihydropyrazin-2-one 4-oxide
(52) 3-Isobutyl-5-methoxy-6-[4-(3-methoxy-4-hydroxycinnamoyl)-1-piperazinyl]carbonyl-1,2-dihydropyrazin-2-one 4-oxide
(53) 3-Isobutyl-5-methoxy-6-(3,4,5-trimethoxy-benzyl)-1,2-dihydropyrazin-2-one 4-oxide
(54) 3-Isobutyl-5-methoxy-6-benzyl-1,2-dihydropyrazin-2-one 4-oxide
(55) 3-Isobutyl-5-methoxy-6-(3,5,-di-tert-butyl-4-hydroxybenzyl)-1,2-dihydropyrazin-2-one 4-oxide
(56) 3-Isobutyl-5-ethoxy-6-(3,4,5-trimethoxy-benzyl)-1,2-dihydropyrazin-2-one 4-oxide
(57) 3-Isobutyl-5-ethyl-6-(3,4,5-trimethoxybenzyl)-1,2-dihydropyrazin-2-one 4-oxide
(58) 3-Isobutyl-5-methoxy-6-[4-(3-methoxyphenyl)-1-piperazinyl]carbonyl-1,2-dihydropyrazin-2-one 4-oxide Pharmacological Test - 1

Inhibitory effect against superoxide radicals released from the peritoneal macrophage cells of guinea pig by stimulation:

Mineral oil (15 ml) was intraperitoneally administered to a guinea pig, then 96 hours after the administration, the peritoneal macrophage cells were sampled.

Superoxide radicals ($O_2^-$) were determined by means of reduction of cytochrome C method according to the procedure described in an article written by T. Matsumoto, K. Takeshige and S. Minakami: *Biochemical and Biophysical Research Communications*, Vol. 88, No. 3, pp. 974–979, (1979).

The peritoneal macrophage cells were added to make the final concentration of $2\times10^6$ cells/ml into ml of 80 µM-cytochrome C solution, and the test compound of pyrazine derivative of the present invention was added thereto to make the test group sample. On the other hand, water was added in place of the test compound of the present invention to make the control group sample. Each of the test group sample and the control group sample was subjected to pre-incubation at 37° C. for 1 minute.

As to the stimulating agent for releasing superoxide radicals ($O_2^-$), FMLP (formylmethionyl leucyl phenylalanine) was added to make the final concentration thereof to $10^{-7}$ M, to each of the test group sample and the control group sample. Then both samples were subjected to additional reaction by incubation for 1 minute.

Difference of the optical absorbances measured at 550 nm ($OD_{550}$) of both test group and control group samples were determined, and the 50% inhibitory concentration ($IC_{50}$) was obtained by calculating as the ratio of $OD_{550}$ of the test group sample to that of the control group sample. The $IC_{50}$ ($\times 10^{-6}$ g/ml) values obtained from the test are shown in Table 3 as follows:

TABLE 3

| Test compound No. | $IC_{50}$ ($\times 10^{-6}$ g/ml) |
|---|---|
| 1 | 30 |
| 2 | 40 |
| 3 | 20 |
| 4 | 56 |
| 5 | 17 |
| 6 | 3 |
| 7 | 18 |
| 8 | 10 |
| 9 | 7 |
| 10 | 25 |
| 11 | 15 |
| 12 | 40 |
| 13 | 20 |
| 14 | 3 |
| 15 | 5 |
| 16 | 27 |
| 17 | 35 |
| 18 | 5 |
| 19 | 10 |
| 20 | 10 |
| 21 | 50 |
| 22 | 40 |
| 23 | 25 |
| 24 | 2 |
| 25 | 6 |
| 26 | 20 |
| 27 | 15 |
| 28 | 7 |
| 29 | 11 |
| 32 | 6 |
| 34 | 3 |
| 35 | 20 |
| 36 | 20 |
| 37 | 20 |
| 38 | 5 |
| 39 | 20 |

TABLE 3-continued

| Test compound No. | IC$_{50}$ (× 10$^{-6}$ g/ml) |
|---|---|
| 40 | 8 |
| 41 | 10 |
| 45 | 30 |
| 46 | 4 |
| 47 | 3 |
| 48 | 20 |
| 49 | 20 |
| 53 | 5 |
| 54 | 11 |
| 55 | 5 |
| 56 | 5 |
| 57 | 15 |

Pharmacological Test - 2

Inhibitory effect against the releasing of lysosome from the neutrocytes of rat

The neutrocytes of rat were sampled from the abdominal cavity of the rat 16 hours after the administration of 10 ml of 1%-casein solution (physiological saline solution).

Reaction of the releasing of lysosome from the neutrocytes of rat was determined by means of the method as described in an article written by T. Matsumoto, K. Takeshige and S. Minakami: *Biochemical and Biophysical Research Communications*, Vol. 88, No. 3, pp. 974–979, (1979).

The neutrocytes being sampled were added to Hank's solution so as to make the concentration thereof as 5×10$^5$ cells/ml, and the test compound of pyrazine derivative of the present invention was added thereto to make the test group sample. On the other hand, water as added in place of the pyrazine derivative of the present invention to make the control group sample. Each of the test group sample and the control group sample was subjected to pre-incubation at 37° C. for 1 minute.

As to the stimulating agents, 10$^{-6}$M of FMLP (formylmethionyl leucyl phenylalanine) and 5 μg/ml of cytochalasin B were added to the solution. Thus, obtained mixture of the solution was reacted by incubating for 15 minutes. After the incubation, the mixture of the solution was subjected to centrifugation at 2,000 rpm for 10 minutes. The supernatant (0.2 ml) was admixed with 0.5 ml of 0.1M-acetic acid buffer solution (pH 4.5) in which 0.3 mM of phenolphthalein glucuronic acid was dissolved. Then the resulting mixture of the solutions was reacted at 37° C. for 5 hours by incubation. After the reaction, 1N-NaOH solution was added to the reaction mixture so as to make the pH value thereof to pH 8 to 9, and the optical absorbance of both test group samples and control group samples were determined at 540 nm (OD$_{540}$).

The 50% inhibitory concentration (IC$_{50}$) values were obtained by calculation as the ratio of OD$_{540}$ of the test group samples to that of the control group samples. The IC$_{50}$ (×10$^{-6}$ g/ml) values obtained from the test are shown in Table 4 as follows.

TABLE 4

| Test compound No. | IC$_{50}$ (× 10$^{-6}$ g/ml) | Test compound No. | IC$_{50}$ (× 10$^{-6}$ g/ml) |
|---|---|---|---|
| 6 | 20 | 35 | 30 |
| 7 | 16 | 36 | 30 |
| 9 | 25 | 38 | 30 |
| 17 | 16 | 41 | 30 |
| 28 | 30 | 43 | 20 |
| 29 | 10 | 47 | 10 |
| 30 | 30 | 51 | 30 |
| 31 | 30 | 54 | 50 |
| 32 | 10 | | |

Pharmacological Test - 3

Inhibitory effect against the releasing of hydrogen peroxide (H$_2$O$_2$) from the neutrocytes of rat abdominal cavity 1) 1%-Casein solution was administered to the adbominal cavity of a SD-strain rat, then 16 hours after the administration, the neutrocytes were obtained by washing the abdominal cavity. Thus obtained neutrocytes were washed with Hank's solution.

2) The formulation of the reaction mixture(*) was as follows:

| | |
|---|---|
| NaN$_3$ | 1 mM |
| NaCl | 140 mM |
| Glucose | 5.5 mM |
| Phenol red | 0.28 mM |
| Horse Radish peroxidase | 8.5 U/ml |
| HEPES (pH 7.0) | 10 mM |
| Rat neutrocytes | 10$^6$ cells/ml |
| FMLP | 2 × 10$^{-6}$M |
| KCl | 5 mM |
| MgCl$_2$ | 1 mM |
| CaCl$_2$ | 1 mM |

Text compound was added to the reaction mixture, then the whole mixture was incubated at 37° C. for 1 hour.

3) Next, the reacted mixture was subjected to centrifugal separation at 2,000 rpm for 10 minutes, then ml of the supernatant liquor was taken as a sample and microliters of 1N-NaOH solution was added thereto.

4) The optical absorbance at 510 nm (OD$_{510}$) was determined by means of using a spectrophotometer. The 50% inhibitory concentration was obtained by calculating as the ratio of OD$_{510}$ of the test group sample to that of the control group sample. The results are indicated in Table 5 as follows:

TABLE 5

| Test compound No. | IC$_{50}$ (× 10$^{-5}$ g/ml) | Test compound No. | IC$_{50}$ (× 10$^{-5}$ g/ml) |
|---|---|---|---|
| 30 | <0.3 | 50 | 0.5 |
| 33 | <0.3 | 51 | 0.5 |
| 34 | 1.0 | 52 | 0.3 |
| 38 | 3.0 | 55 | 0.5 |
| 42 | 0.6 | 57 | 3.0 |
| 43 | 0.8 | 5 | 6 |
| 44 | 3.0 | 20 | <6 |
| 46 | 5.0 | | |

(*) A. Sodhi, et al: Int. J. Immunopharmac., Vol. 8, No. 7, pp. 709–714, (1986)

Pharmacological Test - 4

Induction of Heymann nephritis

1) Test animals and sampling of the antiserum:

SD-strain male rats (7 week old, 200–230 g body weight) were used as test animals.

The antiserum which induces passive Heymann nephritis was prepared by procedures according to the method of T. S. Edington, et al. (**) as follows.

First, the antigen (FX1A fraction) of venaltubular brush border was sampled from the SD rat. Next, the antigen was admixed with Freund's complete adjuvant, then a New Zealand White rabbit was sensitized therewith. Then, sensitizations were conducted 3 times in every 2 weeks, and 2 weeks after the final sensitization, the blood was sampled.

2) Induction of Heymann nephritis and method of experiment:

The test rats were divided into test groups each of which consisting of 7 rats(**).

Heymann nephritis of the rate were induced by injecting the antiserum to the tail vein of the rats. The test compound was suspended in 0.5%-CMC (carboxymethylcellulose) aqueous solution, and was continuously orally administered for 7 days once a day from the fourth day after the injection. The urine samples were taken from the test rats time sequentially at the 11th day after the injection, and then amount of protein in the urine samples were determined.

The results are shown in Table 6 as follows:

TABLE 6

| Test compound No. | Dosage (mg/kg/day) | Amount of protein in the 12th day's urine sample (mg/day) | Inhibition rate (%) |
| --- | --- | --- | --- |
| Control | — | 351.5 + 23.3 | — |
| 58 | 20 | 179.2 + 26.3 | 49.0% |

(**) T. S. Edington, R. J. Glassock and F. J. Dixon: Autologous immune complex nephritis induced with renal tubular antigen. I. Identification and isolation of the pathogenetic antigen. J. Exp. Med. Vol. 127, pp. 555–572 (1968)

What is claimed is:

1. Pyrazine compounds and pharmaceutically acceptable salts thereof of the formula,

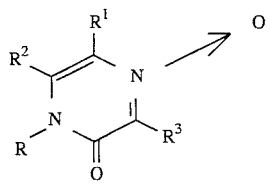

wherein R is a hydrogen atom;
R$^1$ is a lower alkoxy group or a lower alkyl group;
R$^3$ is a lower alkyl group or a lower alkenyl group; and
R$^2$ is a group of the formula

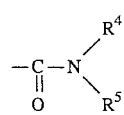

wherein R$^4$ and R$^5$ form with the nitrogen atom to which R$^4$ and R$^5$ are directly bonded thereto, an unsubstituted piperazinyl or an unsubstituted pyrazinyl group or a substituted piperazinyl or a substituted pyrazinyl group having as a substiuent: an oxo group; a lower alkoxycarbonyl group; a pyridyl group; an unsubstituted pyrazinylcarbonyl group; a substituted pyrazinylcarbonyl group having on the pyrazine ring from 1 to 4 substituents selected from the group consisting of an oxo group and a lower alkyl group; an unsubstituted phenyl group; a substituted phenyl group having on the phenyl ring from 1 to 3 substituents selected from the group consist consisting of a lower alkoxy group, a lower alkyl group and a lower alkanoyl group; an unsubstituted benzoyl group; a substituted benzoyl group having on the phenyl ring from 1 to 3 substituents selected from the group consisting of a lower alkoxy group and a hydroxy group; a substituted benzoyl group having on the phenyl ring a lower alkylenedioxy group as a substituent; an unsubstituted phenyl-lower alkyl group; a substituted phenyl-lower alkyl group having on the phenyl ring from 1 to 3 substituents selected from the group consisting of a lower alkoxy group and a halogen atom; an unsubstituted phenyl-lower alkenylcarbonyl group; or a substituted phenyl-lower alkenylcarbonyl group having on the phenyl ring from 1 to 3 substituents selected from the group consisting of a hydroxy group and a lower alkoxy group.

2. The pyrazine compounds and pharmaceutically acceptable salts thereof of claim 1, wherein R$^1$ is a lower alkoxy group.

3. The pyrazine compounds and pharmaceutically acceptable salts thereof of claim 1, wherein R$^1$ is a lower alkyl group.

4. The pyrazine compounds and pharmaceutically acceptable salts thereof of claim 2, wherein R$^3$ is a lower alkyl group.

5. The pyrazine compounds and pharmaceutically acceptable salts thereof of claim 2, wherein R$^3$ is a lower alkenyl group.

6. The pyrazine compounds and pharmaceutically acceptable salts thereof of claim 3, wherein R$^3$ is a lower alkyl group.

7. The pyrazine compounds and pharmaceutically acceptable salts thereof of claim 3, wherein R$^3$ is a lower alkenyl group.

8. The pyrazine compounds and pharmaceutically acceptable salts thereof of claim 4, wherein R$^2$ is a group of the formula

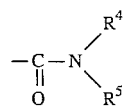

and R$^4$ and R$^5$ form, with the nitrogen atom to which R$^4$ and R$^5$ are directly bonded thereto, an unsubstituted or a substituted piperazinyl group.

9. The pyrazine compounds and pharmaceutically acceptable salts thereof of claim 5, wherein R$^2$ is a group of the formula

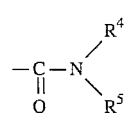

and R$^4$ and R$^5$ form, with the nitrogen atom to which R$^4$ and R$^5$ are directly bonded thereto, an unsubstituted or a substituted piperazinyl group.

10. The pyrazine compounds and pharmaceutically acceptable salts thereof of claim 6, wherein R$^2$ is a group of the formula

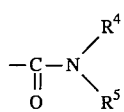

and $R^4$ and $R^5$ form, with the nitrogen atom to which $R^4$ and $R^5$ are directly bonded thereto, an unsubstituted or a substituted piperazinyl group.

11. The pyrazine compounds and pharmaceutically acceptable salts thereof of claim 7, wherein $R^2$ is a group of the formula

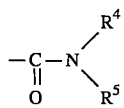

and $R^4$ and $R^5$ form, with the nitrogen atom to which $R^4$ and $R^5$ are directly bonded thereto, an unsubstituted or a substituted piperazinyl group.

12. 3-Isobutyl-5-methoxy-6-[4-(3-methoxyphenyl)-1-piperazinyl] carbonyl-1,2-dihydropyrazine-2-one 4-oxide.

13. A pharmaceutical composition for treating autoimmune diseases, arteriosclerosis, ischemic heart diseases, ischemic cerebral disturbances, hepatic insufficiency and renal insufficiency which are caused by superoxide radical, and for treating nephritis, containing an effective amount of a pyrazine compound or pharmaceutically acceptable salt thereof of claim 1 as the active ingredient and a pharmaceutically acceptable carrier.

* * * * *